(12) United States Patent
Kiani et al.

(10) Patent No.: US 9,333,345 B2
(45) Date of Patent: May 10, 2016

(54) ELECTRICAL STIMULATION FOR A FUNCTIONAL ELECTRICAL STIMULATION SYSTEM

(71) Applicants: Farsad Kiani, Richmond Hill (CA); Elias Koikas, Toronto (CA); Qiang Song, Markham (CA); Jinbiao Zheng, Scarborough (CA); Edgardo Zaragoza, Scarborough (CA); Arthur Kwok, Markham (CA)

(72) Inventors: Farsad Kiani, Richmond Hill (CA); Elias Koikas, Toronto (CA); Qiang Song, Markham (CA); Jinbiao Zheng, Scarborough (CA); Edgardo Zaragoza, Scarborough (CA); Arthur Kwok, Markham (CA)

(73) Assignee: Ensilver Canada, Markham (CA)

( * ) Notice: Subject to any disclaimer, the term of this patent is extended or adjusted under 35 U.S.C. 154(b) by 0 days.

(21) Appl. No.: 14/506,176

(22) Filed: Oct. 3, 2014

(65) Prior Publication Data

US 2015/0100107 A1    Apr. 9, 2015

Related U.S. Application Data

(60) Provisional application No. 61/886,134, filed on Oct. 3, 2013.

(51) Int. Cl.
*A61N 1/36*   (2006.01)
*A61N 1/378*  (2006.01)
*A61B 5/0488* (2006.01)
(Continued)

(52) U.S. Cl.
CPC .......... *A61N 1/36003* (2013.01); *A61B 5/0488* (2013.01); *A61B 5/04888* (2013.01); *A61B 5/1112* (2013.01); *A61B 5/6828* (2013.01); *A61N 1/378* (2013.01); *A61N 1/36014* (2013.01)

(58) Field of Classification Search
CPC ................................................. A61N 1/36003
See application file for complete search history.

(56) References Cited

U.S. PATENT DOCUMENTS 5,014,705 A    5/1991   Graupe et al.
5,016,635 A    5/1991   Graupe
(Continued)

FOREIGN PATENT DOCUMENTS

CA    2074532 A1    5/1992
CA    2794533 A1    5/2007
(Continued)

OTHER PUBLICATIONS

Bioness Inc., "Bioness LiveOn NESS H200 Wireless: User's Guide", 2011.
(Continued)

*Primary Examiner* — Kennedy Schaetzle
(74) *Attorney, Agent, or Firm* — Bereskin & Parr LLP/ S.E.N.C.R.L., s.r.l.; Tony R. Orsi

(57) ABSTRACT

An electrical stimulation system and method for generating a stimulation signal for at least two electrodes coupled to a body part in a functional electrical stimulation system. One example embodiment includes a controller unit operable for receiving stimulation parameters and a trigger signal, and in response to receiving the trigger signal, outputting control signals based on the stimulation parameters. A voltage conversion module coupled to the unit receives the control signals and converts a supply voltage based on the received control signals. A switch receives the converted supply voltage at a first terminal and outputs a simulation signal at a second terminal. Outputting of the converted supply voltage at the second terminal by the switch is controlled by a driver module based on the received control signals.

32 Claims, 21 Drawing Sheets

(51) Int. Cl.
*A61B 5/00* (2006.01)
*A61B 5/11* (2006.01)

(56) References Cited

U.S. PATENT DOCUMENTS

| | | | |
|---|---|---|---|
| 5,070,873 | A | 12/1991 | Graupe et al. |
| 5,092,329 | A | 3/1992 | Graupe et al. |
| 6,324,432 | B1 | 11/2001 | Rigaux et al. |
| 6,456,884 | B1 | 9/2002 | Kenney |
| 7,147,667 | B2 | 12/2006 | Bedard |
| 7,632,239 | B2 | 12/2009 | Dar et al. |
| 7,660,636 | B2 | 2/2010 | Castel et al. |
| 7,867,284 | B2 | 1/2011 | Bedard |
| 7,899,556 | B2 | 3/2011 | Nathan et al. |
| 7,949,403 | B2 | 5/2011 | Palermo et al. |
| 8,057,486 | B2 | 11/2011 | Hansen |
| 8,082,035 | B2 | 12/2011 | Glukhovsky |
| D658,769 | S | 5/2012 | Moser et al. |
| 8,167,640 | B2 | 5/2012 | Ochoa et al. |
| 8,175,713 | B1 * | 5/2012 | Cywinski ............ A61H 39/002 607/48 |
| 8,209,022 | B2 | 6/2012 | Dar et al. |
| 8,209,036 | B2 | 6/2012 | Nathan et al. |
| 8,332,029 | B2 | 12/2012 | Glukhovsky et al. |
| 8,364,277 | B2 | 1/2013 | Glukhovsky |
| 8,382,688 | B2 | 2/2013 | Dar et al. |
| 8,463,390 | B2 * | 6/2013 | Muraoka ............ A61N 1/36014 607/48 |
| 2003/0125781 | A1 * | 7/2003 | Dohno ............ A63B 21/00181 607/75 |
| 2003/0195586 | A1 | 10/2003 | Rigaux et al. |
| 2003/0195587 | A1 | 10/2003 | Rigaux et al. |
| 2004/0122483 | A1 | 6/2004 | Nathan et al. |
| 2005/0261609 | A1 | 11/2005 | Collings et al. |
| 2009/0030344 | A1 | 1/2009 | Moser et al. |
| 2009/0240313 | A1 | 9/2009 | Buhlmann |
| 2010/0042180 | A1 | 2/2010 | Mueller et al. |
| 2010/0191316 | A1 | 7/2010 | Buhlmann et al. |
| 2011/0093035 | A1 | 4/2011 | Moser et al. |
| 2011/0125290 | A1 | 5/2011 | Langlois |
| 2011/0137429 | A1 | 6/2011 | Bedard |
| 2011/0152968 | A1 | 6/2011 | Nathan et al. |
| 2011/0282412 | A1 | 11/2011 | Glukhovsky et al. |
| 2012/0059298 | A1 | 3/2012 | Hoffman et al. |
| 2012/0116478 | A1 | 5/2012 | Buhlmann et al. |
| 2012/0203156 | A1 | 8/2012 | Dar et al. |
| 2012/0239112 | A1 * | 9/2012 | Muraoka ............ A61N 1/36014 607/49 |
| 2012/0330375 | A1 | 12/2012 | Nathan et al. |
| 2012/0330394 | A1 | 12/2012 | Dar et al. |
| 2012/0330395 | A1 | 12/2012 | Dar et al. |
| 2013/0013041 | A1 | 1/2013 | Glukhovsky et al. |
| 2014/0259799 | A1 | 9/2014 | Mcdonnell, Jr. et al. |
| 2015/0100104 | A1 | 4/2015 | Kiani et al. |
| 2015/0100105 | A1 | 4/2015 | Kiani et al. |

FOREIGN PATENT DOCUMENTS

| | | |
|---|---|---|
| CA | 2649663 A1 | 11/2007 |
| CA | 2663030 A1 | 4/2008 |
| CA | 2697381 A1 | 2/2009 |
| CA | 2727812 A1 | 12/2009 |
| CA | 2732751 A1 | 2/2010 |
| CA | 2780328 A1 | 6/2011 |
| CA | 2782677 A1 | 6/2011 |
| CN | 202078650 U | 12/2011 |
| DE | 60 2004 005 692 T2 | 12/2007 |
| EP | 1201266 A1 | 5/2002 |
| EP | 1435891 A4 | 4/2003 |
| EP | 1530493 A1 | 3/2004 |
| EP | 1819395 A2 | 6/2006 |
| EP | 1874398 A4 | 10/2006 |
| EP | 1874404 A2 | 10/2006 |
| EP | 2037804 A2 | 12/2007 |
| EP | 1095670 B1 | 5/2008 |
| EP | 2120801 A1 | 7/2008 |
| EP | 1531767 B1 | 10/2008 |
| EP | 1980224 A2 | 10/2008 |
| EP | 2152359 A2 | 12/2008 |
| EP | 2180918 A1 | 2/2009 |
| EP | 2194862 A1 | 3/2009 |
| EP | 2247249 A1 | 8/2009 |
| EP | 2252242 A1 | 8/2009 |
| EP | 2291220 A1 | 12/2009 |
| EP | 2320993 A1 | 2/2010 |
| EP | 2506918 A1 | 6/2011 |
| EP | 2506919 A1 | 6/2011 |
| EP | 2392381 A2 | 12/2011 |
| EP | 1531766 B1 | 1/2012 |
| EP | 2097851 B1 | 2/2012 |
| EP | 2012669 B1 | 3/2013 |
| EP | 2586489 A1 | 5/2013 |
| JP | 201275933 A | 4/2012 |
| KR | 10-2005-0042793 A | 5/2005 |
| KR | 10-2005-0058417 A | 6/2005 |
| KR | 10-2006-0100427 A | 9/2006 |
| KR | 10-2009-0025184 A | 3/2009 |
| WO | 9209328 A1 | 6/1992 |
| WO | 2005-122740 A3 | 12/2005 |
| WO | 2006-061804 A8 | 6/2006 |
| WO | 2006-113802 A2 | 10/2006 |
| WO | 2007-125534 A2 | 11/2007 |
| WO | 2008-043065 A2 | 4/2008 |
| WO | 2008-086629 A1 | 7/2008 |
| WO | 2009-021157 A1 | 2/2009 |
| WO | 2009-026588 A2 | 2/2009 |
| WO | 2009-038861 A1 | 3/2009 |
| WO | 2009-052134 A1 | 4/2009 |
| WO | 2009-052135 A1 | 4/2009 |
| WO | 2009-088563 A1 | 7/2009 |
| WO | 2009-137234 A2 | 11/2009 |
| WO | 2009-155436 A1 | 12/2009 |
| WO | 2009-158389 A1 | 12/2009 |
| WO | 2010-002517 A1 | 1/2010 |
| WO | 2010-017004 A1 | 2/2010 |
| WO | 2010-107648 A1 | 9/2010 |
| WO | 2011-068823 A1 | 6/2011 |
| WO | 2011-068849 A1 | 6/2011 |
| WO | 2013-001526 A2 | 6/2012 |
| WO | 2012-107921 A1 | 8/2012 |
| WO | 2012-150500 A1 | 11/2012 |

OTHER PUBLICATIONS

Bioness Inc., "Bioness LiveOn Ness L300Plus: User's Guide", 2011.
Bioness Inc., "Bioness LiveOn Ness L300: Clinician's Guide", 2010.
Innovative Neurotronics, "WalkAide System: User Manual", 2010.
Co-pending Patent U.S. Appl. No. 14/529,854, filed on Oct. 31, 2014, entitled "Cuff Unit for a Functional Electrical Stimulation (FES) Orthotic System".

* cited by examiner

ELECTRICAL STIMULATION FOR A FUNCTIONAL ELECTRICAL STIMULATION SYSTEM

CROSS REFERENCE TO RELATED APPLICATION

The present application claims priority from provisional patent application No. 61/886,134, filed Oct. 3, 2013 and entitled "ELECTRICAL STIMULATION FOR A FUNCTIONAL ELECTRICAL STIMULATION SYSTEM", the disclosure of which is hereby incorporated by reference in its entirety.

FIELD

The described embodiments relate to electrical stimulation for a Functional Electrical Stimulation (FES) system, and more particularly are related to electrical stimulation devices and methods that may be used to generate a stimulation signal in a power-efficient manner.

INTRODUCTION

Individuals suffering from a central nervous system injury, such as a stroke, a brain injury, multiple sclerosis, cerebral palsy or partial spinal cord injuries, or other medical conditions may have mobility problems due to that injury or medical condition. Functional electrical stimulation (FES) systems may assist those individuals address those mobility problems.

Existing FES systems provide electrical stimulation to muscles that may have been paralyzed or otherwise affected due to the central nervous system injury or other medical conditions. The electrical stimulation may facilitate motion in those affected muscles. In some cases, FES systems may also help reeducate muscle movement, retard atrophy of any affected muscles due to disuse, and maintain or increase a range of motion at nearby joints.

An example application of an FES system is to enhance ankle dorsiflexion for individuals experiencing foot drop. Foot drop is a gait abnormality that stems from a weakness in a foot, damage to a peroneal nerve, or paralysis of muscles in an anterior portion of a lower leg. Foot drop may be caused by various conditions, such as muscle or spinal nerve trauma, abnormal anatomy, toxins and disease. Individuals affected by foot drop are unable to lift their foot and toes during a swing phase of their gait thereby causing their toes to be caught by the ground and their foot to drag on the ground. The FES system can assist those individuals by sending electrical stimulation signals to the affected muscles during the swing phase of their gait in order to trigger movement in those muscles so that the foot is lifted and not dragged along the ground.

Although existing FES systems are generally portable, they tend to be bulky and therefore, cumbersome for users to carry around on a daily basis. Existing FES systems also tend to lack versatility in operation and offer limited functionality.

SUMMARY

In a broad aspect, at least one embodiment described herein provides an electrical stimulation system for generating a stimulation signal for at least two electrodes for stimulating a body part in a functional electrical stimulation system. The electrical stimulation system includes a controller unit operable for receiving at least one set of stimulation parameters, receiving a trigger signal; and in response to receiving the trigger signal, outputting at least a first control signal and a second control signal based on the at least one set of stimulation parameters, a voltage conversion module coupled to the controller unit, the voltage conversion module being configured to receive at least the first control signal and converting a supply voltage based on the received first control signal, and at least one switch receiving the converted supply voltage at a first terminal and being configured to selectively output based on the second control signal a stimulation signal at a stimulation output terminal.

In at least one embodiment, the electrical stimulation system may further comprise a driver module controlling the at least one switch based on at least the second control signal, wherein the at least one switch is configured to output the converted voltage as the stimulation signal at the output terminal when the driver module configures the at least one switch to a closed position.

In at least one embodiment, at least one set of stimulation parameters may comprise a desired amplitude of the stimulation signal and wherein the first control signal may be adjusted based on the desired amplitude to correspondingly control certain parameters of the voltage conversion module.

In at least one embodiment, at least one set of stimulation parameters may further comprise a desired rise time, a desired hold time, a desired drop time, and a desired idle time of a cycle of the stimulation signal and wherein the first control signal may be adjusted based on the desired rise time, desired hold time, desired drop time and desired idle time.

In at least one embodiment, the voltage conversion module may comprise a DC/DC voltage converter having a feedback terminal and an output terminal to output the converted voltage; a feedback resistor coupling the voltage output terminal with the feedback terminal; and a variable resistor coupling the feedback terminal to a reference; and wherein the converted voltage is based on the resistance value of the feedback resistor and the resistance value of the variable resistor.

In at least one embodiment, the first control signal may comprise a value of the variable resistor for outputting the desired amplitude of the stimulation signal and wherein the value of the variable resistor is varied in time according to the received first control signal.

In at least one embodiment, at least one set of stimulation parameters may further comprise a desired period and a desired pulse width of the stimulation signal and wherein the second control signal may be adjusted based on the desired period and pulse width.

In at least one embodiment, the at least one switch may comprise a MOSFET switch and the driver comprises a MOSFET driver.

In at least one embodiment, the voltage conversion module may be configured to convert the supply voltage to a positive converted voltage and a negative converted voltage; and wherein the at least one switch may comprise a first switch configured to receive the positive converted voltage and selectively outputting based on the second control signal the positive converted voltage at an output terminal; and a second switch configured to receive the negative converted voltage and selectively outputting based on the second control signal the negative converted voltage at the output terminal.

In at least one embodiment, the controller unit may be configured to operate as a finite state machine having at least an inter pulse state, a positive pulse state, and a negative pulse state, wherein in the positive pulse state the controller unit may be configured to output the second control signal to configure the first switch to the closed position and maintain the second switch in the open position to output a positive pulse in the stimulation signal; in the negative pulse state the controller unit may be configured to output the second control signal to configure the second switch to the closed position and maintain the first switch in the open position to output a negative pulse in the stimulation signal; and in the inter pulse state the controller unit may be configured to output the first and second control signals to maintain the first switch in the open position and the second switch in the open position to output no pulses in the stimulation signal.

In at least one embodiment, when the first switch is closed the second switch is opened to output the positive converted voltage as the stimulation signal and wherein when the second switch is closed the first switch is opened to output the negative converted voltage as the stimulation signal.

In at least one embodiment, the voltage conversion module may comprise a dual DC/DC converter that is configured to output the positive converted voltage from a first output terminal and the negative converted voltage from a second output terminal; wherein the first output terminal is coupled to a first feedback terminal of the convertor via a first feedback resistor, the first feedback terminal being further coupled to a reference voltage via a first variable resistor, and the positive converted voltage is based on the resistance value of the first feedback terminal and the resistance value of the first variable resistor; and wherein the second output terminal is coupled to a second feedback terminal of the convertor via a second feedback resistor, the second feedback terminal being further coupled to the reference voltage via a second variable resistor, and the negative converted voltage being based on the resistance value of the second feedback terminal and the resistance value of the second variable resistor.

In at least one embodiment, the at least one set of stimulation parameters may comprise a desired pulse width of the stimulation signal and wherein the second control signal may be adjusted based on the desired pulse width; wherein the first switch outputs the positive converted voltage at the output terminal for a duration of time corresponding to the desired pulse width; and wherein the second switch outputs a negative discharging pulse immediately after the first switch completes outputting the positive converted voltage, whereby the negative discharging pulse shortens a voltage fall time at the output terminal.

In at least one embodiment, the width of the negative discharging pulse may be chosen based on the amplitude of the positive converted voltage outputted by the first switch, the width of the negative discharging pulse being shorter than the desired pulse width.

In at least one embodiment, the at least one set of stimulation parameters may comprise a desired amplitude, a desired rise time, a desired hold time, a desired drop time, and a desired idle time of a cycle of the stimulation signal; and wherein a plurality of negative discharging pulses may be defined in the second control signal where each discharging pulse may be defined based on an amplitude of the stimulation signal at a corresponding point in time within the cycle of the stimulation signal.

In at least one embodiment, the second control signal may comprise a first switch control signal for controlling the first switch, the first switch control signal defining a desired period, a desired pulse width, and a plurality of positive discharging pulse widths for a cycle of the stimulation signal; and a second switch control signal for controlling the second switch, the second switch control signal defining a desired period, a desired pulse width, and a plurality of negative discharging pulse widths for a cycle of the stimulation signal; wherein at least one of the first switch control signal and the second switch control signal further defines a phase offset.

In at least one embodiment, the controller unit may be configured to operate as a finite state machine having at least a positive pulse state, a positive discharge state, a negative pulse state, and a negative discharge state wherein in the positive pulse state the controller unit may be configured to output the second control signal to configure the first switch to the closed position and maintain the second switch in the open position to output a positive pulse in the stimulation signal; in the positive discharge state the controller unit may be configured to output the second control signal to open the first switch, immediately close the second switch following opening of the first switch, open the second switch after a duration of time corresponding to a negative discharging pulse width to reduce the fall time of the positive pulse in the stimulation signal; in the negative pulse state the controller unit may be configured to output the second control signal to configure the second switch to the closed position and maintain the first switch in the open position to output a negative pulse in the stimulation signal; and in the negative discharge state the controller unit may be configured to output the second control signal to open the second switch, immediately close the first switch following opening of the second switch, open the first switch after a duration of time corresponding to a positive discharging pulse width to reduce the fall time of the negative pulse in the stimulation signal.

In at least one embodiment, the negative discharging pulse width may be chosen based on the amplitude of the positive converted voltage outputted by the first switch during the previous positive pulse state and wherein the positive discharging pulse width may be chosen based on the amplitude of the negative converted voltage outputted by the second width during the previous negative pulse state.

In at least one embodiment, the first switch may comprise an opto-coupler and the second switch may comprise an opto-coupler.

In at least one embodiment, the voltage fall time at the output terminal may be no more than approximately 50 µs.

In at least one embodiment, the controller unit may further be configured to receive a mode signal indicating that a particular set of the stimulation parameters is to be selected, and wherein the plurality of stimulation control signals may be generated based on the selected set of stimulation parameters.

In at least one embodiment, a change in the trigger signal may indicate a change in the position of the user and that a particular set of the stimulation parameters is to be selected, and wherein the plurality of stimulation control signals may be generated based on the selected set of stimulation parameters.

In another broad aspect, at least one embodiment described herein provides an electrical stimulation system for generating a stimulation signal for at least two electrodes coupled to a body part in a functional electrical stimulation system. The electrical stimulation system includes a controller unit operable for receiving at least one set of stimulation parameters, receiving a trigger signal; and in response to receiving the trigger signal, outputting at least a first control signal and a second control signal based on the at least one set of stimulation parameters, a voltage conversion module coupled to the controller unit, the voltage conversion module being configured to receive at least the first control signal and to convert a supply voltage based on the received first control signal to a positive converted voltage and a negative converted voltage, a first switch configured to receive the positive converted voltage and selectively output based on the second control signal the positive converted voltage at an output terminal, and a second switch configured to receive the negative converted voltage and selectively output based on the second control signal the negative converted voltage at the stimulation output terminal.

In at least one embodiment, the controller unit may be configured to operate as a finite state machine having at least an inter pulse state, a positive pulse state, and a negative pulse state, wherein in the positive pulse state the controller unit may be configured to output the second control signal to configure the first switch to the closed position and maintain the second switch in the open position to output a positive pulse in the stimulation signal; in the negative pulse state the controller unit may be configured to output the second control signal to configure the second switch to the closed position and maintain the first switch in the open position to output a negative pulse in the stimulation signal; and in the inter pulse state the controller unit may be configured to output the first and second control signals to maintain the first switch in the open position and the second switch in the open position to output no pulses in the stimulation signal.

In at least one embodiment, the controller unit may be configured to operate as a finite state machine having at least a positive pulse state, a positive discharge state, a negative pulse state, and a negative discharge state wherein in the positive pulse state the controller unit may be configured to output the second control signal to configure the first switch to the closed position and maintain the second switch in the open position to output a positive pulse in the stimulation signal; in the positive discharge state the controller unit may be configured to output the second control signal to open the first switch, immediately close the second switch following opening of the first switch, open the second switch after a duration of time corresponding to a negative discharging pulse width to reduce the fall time of the positive pulse in the stimulation signal; in the negative pulse state the controller unit may be configured to output the second control signal to configure the second switch to the closed position and maintain the first switch in the open position to output a negative pulse in the stimulation signal; and in the negative discharge state the controller unit is configured to output the second control signal to open the second switch, immediately close the first switch following opening of the second switch, open the first switch after a duration of time corresponding to a positive discharging pulse width to reduce the fall time of the negative pulse in the stimulation signal.

In another broad aspect, at least one embodiment described herein provides a method for generating a stimulation signal for a functional electrical stimulation system. The method includes receiving a selection of a set of stimulation parameters defining characteristics of the stimulation signal to be generated, determining values of a first control signal and a second control signal based on the set of stimulation parameters, outputting the first control signal to control an amplitude of the stimulation signal, determining a state of a finite state machine, and outputting a second control signal based on the state of the state machine, the second control signal being adapted for controlling timing for the stimulation signal.

In at least one embodiment, the set of stimulation parameters may comprise a desired amplitude of the stimulation signal, and the first control signal may be determined based on the desired amplitude.

In at least one embodiment, the set of stimulation parameters may further comprise a desired rise time, a desired hold time, a desired drop time, and a desired idle time of a cycle of the stimulation signal, and the first control signal may be determined based on the desired rise, desired hold time, desired drop time and desired idle time.

In at least one embodiment, the set of stimulation parameters may comprise a desired period and a desired pulse width of the stimulation signal, and the second control signal may be determined based on the desired period and pulse width.

In at least one embodiment, the finite state machine may comprise an inter pulse state, a positive pulse state, and a negative pulse state, wherein in the positive pulse state the second control signal may configure a first switch to a closed position and maintains a second switch in an open position to output a positive pulse in the stimulation signal; in the negative pulse state the second control signal may configure the second switch to the closed position and maintains the first switch in the open position to output a negative pulse in the stimulation signal; and in the inter pulse state the first and second control signals may maintain the first switch in the open position and the second switch in the open position to output no pulses in the stimulation signal.

In at least one embodiment, the finite state machine may comprise a positive pulse state, a positive discharge state, a negative pulse state, and a negative discharge state wherein in the positive pulse state the second control signals may configure a first switch to a closed position and maintains a second switch in an open position to output a positive pulse in the stimulation signal; in the positive discharge state the second control signals may configure the first switch to the open position, immediately configures the second switch to the closed position following the opening of the first switch, and configures the second switch to the open position after a duration of time corresponding to a negative discharging pulse width to reduce the fall time of the positive pulse in the stimulation signal; in the negative pulse state the second control signals configures the second switch to the closed position and maintains the first switch in the open position; and in the negative discharge state the second control signals may configure the second switch to the open position, immediately configures the first switch to the closed position following the opening of the second switch, and configures the first switch to the open position after a duration of time corresponding to a positive discharging pulse width to reduce the fall time of the negative pulse in the stimulation signal.

In another broad aspect, at least one embodiment described herein provides a computer readable medium comprising a plurality of instructions executable on a processor of a device for adapting the processor to implement a method of generating a stimulation signal for a functional electrical stimulation system. The computer readable medium may comprise instructions for receiving a selection of a set of stimulation parameters defining characteristics of the stimulation signal to be generated; determining values of a first control signal and a second control signal based on the set of stimulation parameters; outputting the first control signal to control an amplitude of the stimulation signal; determining a state of a finite state machine; and outputting a second control signal based on the state of the state machine, the second control signal being adapted for controlling timing for the stimulation signal.

In at least one embodiment, the computer readable medium may comprise instructions for performing various suitable aspects of any of the methods described in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

DETAILED DESCRIPTION OF DRAWINGS

For a better understanding of the various embodiments described herein, and to show more clearly how these various embodiments may be carried into effect, reference will be made, by way of example, to the accompanying drawings which show at least one example embodiment, and which are now briefly described.

FIGS. 15-1 and 15-2 illustrates a circuit diagram of an example embodiment of the electrical stimulation system.

FIGS. 16-1 and 16-2 illustrates a circuit diagram of another example embodiment of the electrical stimulation system.

Figure 1:
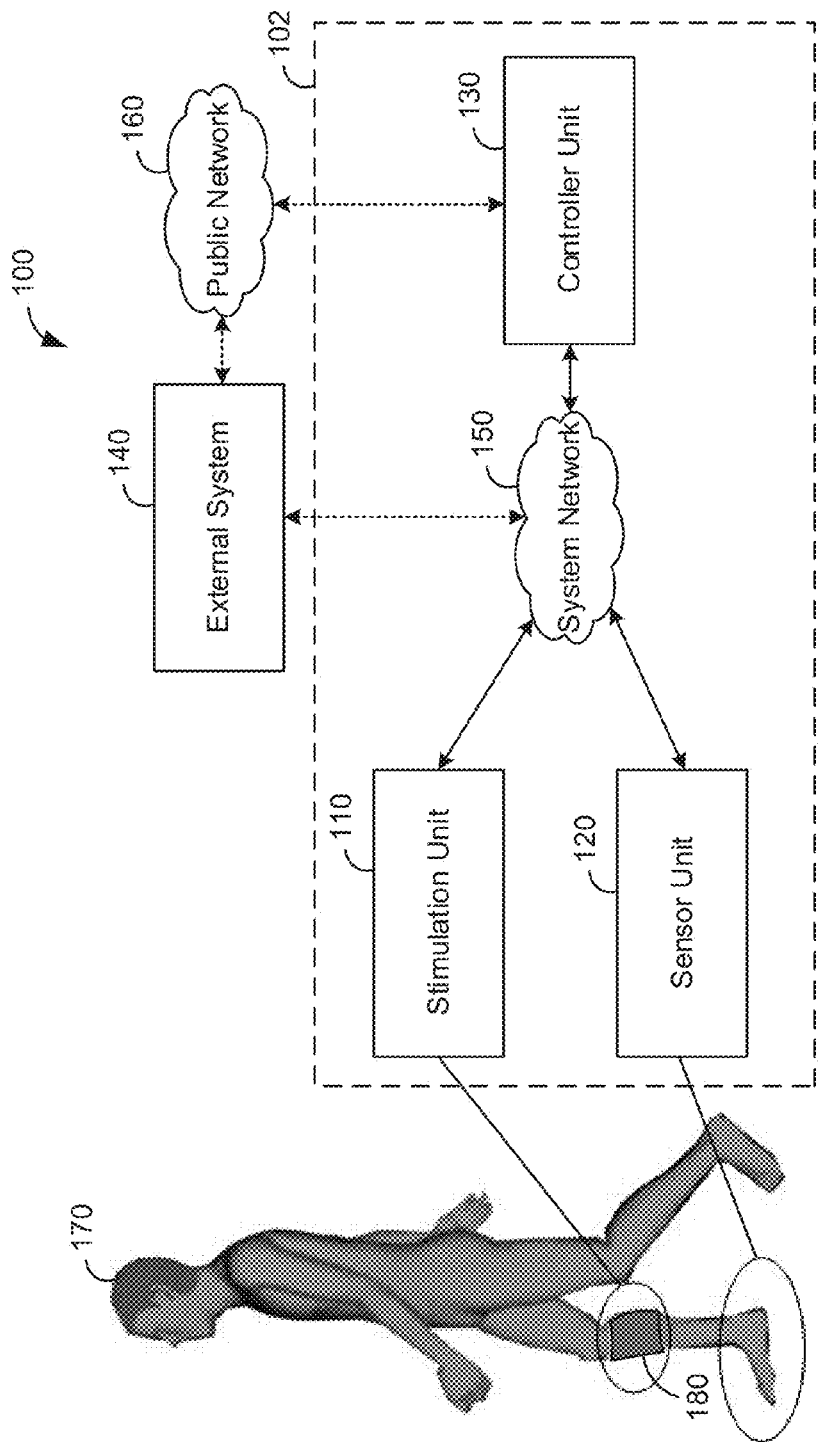
FIG. 1 is a block diagram of components interacting with a functional electrical stimulation (FES) system in accordance with an example embodiment.

Further aspects and advantages of the embodiments described herein will appear from the following description taken together with the accompanying drawings.

DESCRIPTION OF VARIOUS EMBODIMENTS

The various embodiments described herein generally relate to electrical stimulation that can be used with an FES system, and more particularly are related to an electrical stimulation devices and methods that may be used to generate a stimulation signal in a power-efficient manner.

Various apparatuses or processes will be described below to provide an example of an embodiment of the claimed subject matter. No embodiment described below limits any claimed subject matter and any claimed subject matter may cover processes or apparatuses that differ from those described below. The claimed subject matter is not limited to apparatuses or processes having all of the features of any one apparatus or process described below or to features common to multiple or all of the apparatuses or processes described below. It is possible that an apparatus or process described below is not an embodiment of any claimed subject matter. Any subject matter that is disclosed in an apparatus or process described below that is not claimed in this document may be the subject matter of another protective instrument, for example, a continuing patent application, and the applicants, inventors or owners do not intend to abandon, disclaim or dedicate to the public any such claimed subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical element, electrical signal or a mechanical element depending on the particular context.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

At least some of the elements of the systems described that are implemented via software may be written in a high-level procedural language such as object oriented programming or a scripting language. Accordingly, the program code may be written in C, C++, SQL or any other suitable programming language and may comprise modules or classes, as is known to those skilled in object oriented programming. It should also be understood that at least some of the elements of the various systems described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

The computing devices that may be used in the various embodiments described herein generally include at least one processor, a data storage system (including volatile memory or non-volatile memory or other data storage elements or a combination thereof), and at least one communication interface. For example, and without limitation, the programmable devices (referred to herein as computing devices) may be a server, network appliance, an embedded device, a computer expansion module, a personal computer, a laptop, a personal data assistant, a cellular telephone, a smart-phone device, a tablet computer, a wireless device or any other computing device capable of being configured to carry out the methods described herein. The particular embodiment depends on the application of the computing device. For example, a server can be used to provide a centralized database and/or a remote programming interface while an embedded device may be used for components that are worn or otherwise directly used by the user.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform at least some of the functions described herein and to generate output information. The output information may be applied to one or more output devices, in known fashion.

At least some of the programs may be implemented in a high level procedural or object oriented programming and/or scripting language, or both, to communicate with a computer system. However, other programs may be implemented in assembly or machine language, if desired. In any case, the language may be a compiled or interpreted language. The computer programs may be stored on a storage media or a device (e.g. ROM, magnetic disk, optical disc) readable by a general or special purpose programmable device, for configuring and operating the programmable device when the storage media or device is read by the programmable device to perform the procedures described herein. Embodiments of the system may also be considered to be implemented as a non-transitory computer-readable storage medium, configured with a computer program, where the storage medium so configured causes a computing device to operate in a specific and predefined manner to perform the functions described herein.

Furthermore, some of the programs associated with the system, processes and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wireline transmissions, satellite transmissions, internet transmissions (e.g. downloads), media, digital and analog signals, and the like. The computer useable instructions may also be in various formats, including compiled and non-compiled code.

Reference is first made to FIG. 1, which shows a block diagram 100 of components interacting with a functional electrical stimulation (FES) system 102 in accordance with an example embodiment. The FES system 102 generates stimulation signals to assist individuals, such as a user 170 of FIG. 1, with damaged or paralyzed muscles in a lower leg. The FES system 102 may generate stimulation signals for various purposes, such as to facilitate movement of the user 170, to reeducate any affected muscles in the user 170, to retrain the user 170 to walk, or to retard atrophy in muscles due to disuse, for example.

When facilitating movement of the user 170, the FES system 102 can generate stimulation signals to trigger movement at affected muscles. In the case of a user 170 with foot drop, for example, the FES system 102 may generate stimulation signals that are synchronized with a swing phase of a gait of that user 170 in order to help that user 170 lift the foot and prevent the foot from dragging on the ground.

As shown in FIG. 1, the FES system 102 includes a stimulation unit 110, a sensor unit 120 and a controller unit 130. The operation of the stimulation unit 110, the sensor unit 120 and the controller unit 130 will now be further described.

The stimulation unit 110, the sensor unit 120 and the controller unit 130 may communicate with each other via system network 150. As also shown in FIG. 1, the FES system 102 may also communicate with an external system 140 via the system network 150 and/or possibly via a public network 160. As will be described, the FES system 102 may receive signal parameters and other operational instructions from the external system 140 and may also transmit operational data to the external system 140.

Each of the stimulation unit 110, the sensor unit 120 and the controller unit 130 may include a real time calendar and clock (RTCC) component. The RTCC component may require a low frequency crystal or oscillator in order to operate. The RTCC component provides real time date and time information for the FES system 102. The date information may include the year, month, day and week, and the time information may include hours, minutes, and seconds. The RTCC component may continue to operate even when the FES system 102 is in a sleep mode. Therefore, the RTCC component can facilitate system operations in which accurate time information is needed and with minimal power consumption. For example, the RTCC component can help ensure that a timer module at each of the stimulation unit 110, the sensor unit 120 and the controller unit 130 is synchronized so that stimulation signals are triggered at the appropriate time.

The FES system 102 may also enter into a safe mode in response to any communication errors between any two of the stimulation unit 110, the sensor unit 120 and the controller unit 130, as well as between the FES system 102 and the external system 140. For example, when the system network 150 fails to operate properly, the stimulation unit 110 may enter the safe mode and generate a predetermined safe stimulation signal for the user 170, no stimulation signal or provide a warning to the user 170 that a component of the FES system 102 is not functioning properly.

The stimulation unit 110 generates and delivers electrical stimulation signals to the user 170. As shown in FIG. 1, the stimulation unit 110 may be provided in association with a cuff 180 that is worn by the user 170 at a location on the user that is to receive the stimulation signals. In the example of FIG. 1, the cuff 180 is worn on the lower leg of the user 170 to stimulate nerves located in the lower leg. The stimulation unit 110 may include various modules for generating and delivering the stimulation signal to the user 170. It will be understood that the various modules may be hardware, software, and a combination of hardware and software. The stimulation unit 110 may be implemented in several ways as is known by those skilled in the art.

The stimulation unit 110 may generate stimulation signals based on signal parameters stored at the stimulation unit 110 or signal parameters received via the system network 150 from the external system 140 or the controller unit 130. The signal parameters received from the controller unit 130 may be determined based on a variety of factors, including an operational mode of the FES system 102 as selected by the user 170, data provided from waveform data charts and waveform parameters, and stimulation parameters as selected by the user 170 and a third party, such as a doctor or clinician. The signal parameters received from the external system 140 may include stimulation parameters as selected by the third party. In some embodiments, the stimulation unit 110 may vary amplitude or frequency of a stimulation signal based on the signal parameters.

In some embodiments, the stimulation unit 110 may generate multiple stimulation signals to different nerves of the user 170. By stimulating different nerves, different functionalities may be achieved by the FES system 102. The different stimulation signals may be generated at approximately the same time. For example, one to eight stimulation channels may be available at the stimulation unit 110 for generating up to eight stimulation signals. Each stimulation channel may be used for stimulating a different nerve, for example.

To deliver the stimulation signal, the stimulation unit 110 includes at least two electrodes that are positioned substantially around a target nerve that is to receive the stimulation signal. For example, the at least two electrodes may be positioned substantially around a target nerve that is to receive the stimulation signal. Two of the at least two electrodes forms a current path there between over which the stimulation signal travels to stimulate the target nerve. For example, the electrodes may be provided in pairs.

The stimulation unit 110 may also generate operation data, such as stimulation status data, to be displayed at the cuff 180 or by the controller unit 130. For example, the stimulation unit 110 may include a display component, such as an LCD display in some cases.

The sensor unit 120 may include multiple different sensors for detecting data associated with a gait of the user 170 and an environment of the user 170. As shown in FIG. 1, similar to the stimulation unit 110, the sensor unit 120 is generally worn by the user 170. In the example of FIG. 1, the sensor unit 120 is located at the foot of user 170. The sensor unit 120 may be attached to footwear worn by the user 170 or embedded into or otherwise attached to an insole of the user's footwear.

The sensor unit 120 may process at least a portion of the detected sensor data to generate various signal parameters for the stimulation signal. The sensor unit 120 may also transmit the detected sensor data to other components of the FES system 102, such as stimulation unit 110 and controller unit 130, and the external system 140. The detected sensor data may be transmitted in various data formats, such as in a hexadecimal or byte format.

Various sensors may be provided at the sensor unit 120. The sensors may include a force sensor, a temperature sensor, a gyroscope, an accelerometer, and a compass. Different embodiments may include all or different combinations of the aforementioned sensors.

The force sensor can detect an amount of force that it receives. For a sensor unit 120 that is located near or in the insole of the footwear of the user 170, the force sensor can detect the amount of force that is exerted by the foot of the user 170 while the user 170 walks. Based on data collected by the force sensor, the FES system 102 may distinguish between various movements of the user 170, such as whether that user 170 is standing, is in mid-stride or is performing other activities.

The temperature sensor can detect a temperature of an environment of the user 170, for example.

The gyroscope can detect an angular velocity of the sensor unit 120 when the sensor unit 120 is in motion. Based on the detected angular velocity, the FES system 102 may determine an orientation of the sensor unit 120 and therefore an orientation of the foot of the user 170.

The accelerometer can detect an acceleration of the sensor unit 120.

The compass can detect a geomagnetic field of the sensor unit 120 to determine the direction in which the user 170 is walking.

The sensor unit 120 may also track a passage of time with a timer module, and transmit the time data via the system network 150. The sensor unit 120 may track the passage of time to facilitate data collection. For example, the sensor unit 120 may collect sensor data at predetermined time intervals, such as every 10 milliseconds, for example. A timer module may help to trigger data collection at the sensor unit 120. When the FES system 102 is used for addressing foot drop, the sensor unit 120 may track the passage of time to determine a lift period of the foot. The lift period is a period of time from when the user 170 lifts the foot from the ground to when that foot returns to the ground. The lift period may be used for generating the signal parameters for the stimulation signal.

The controller unit 130 can define the signal parameters of the stimulation signal and transmit the signal parameters to the stimulation unit 110 via the system network 150. The controller unit 130 may define the signal parameters based on data received from the sensor unit 120, the external system 140, or parameters stored locally or received at the controller unit 130.

The controller unit 130 is generally carried or worn by the user 170. The controller unit 130 may be a controller device dedicated for use with the FES system 102. The controller unit 130 may be attached to a waist of user 170, for example. The controller device includes hardware and software modules for operating and interacting with each of the other units in the FES system 102 as well as external system 140. The controller device 200 may include one or more different user input controls for receiving input from the user 170, such as a mode button 210.

The controller unit 130 may also be provided as a controller software module that is installed onto existing computing devices that are carried by the user 170. The computing devices may include, but are not limited to, an electronic tablet device, a personal computer, a portable computer, a mobile device, a personal digital assistant, a laptop, a smart phone, a WAP phone, a handheld interactive television, handheld video display terminals, gaming consoles, and other portable electronic devices, for example. The controller software module may include one or more software modules for operating and interacting with each of the other units in the FES system 102 as well as the external system 140.

Figure 2:
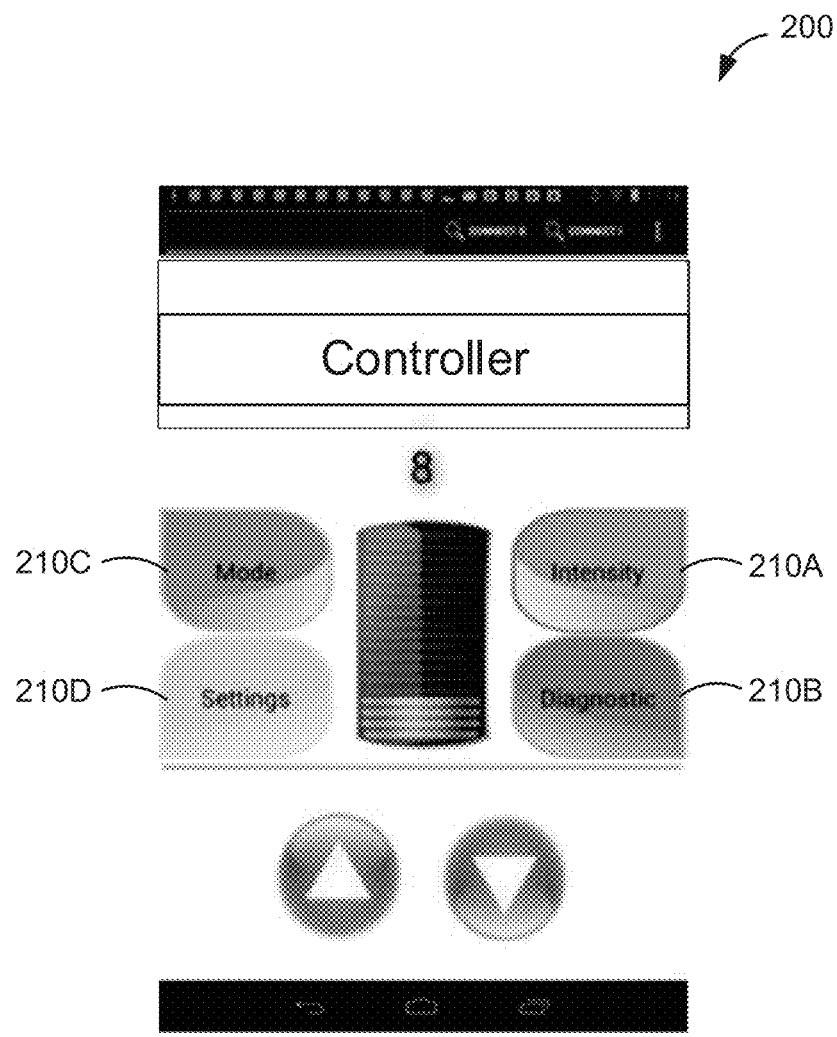
FIG. 2 illustrates an example embodiment of a user interface for a controller unit of the FES system.

In at least some embodiments, the controller unit 130 provides a user control interface from which to receive user inputs for operating the FES system 102. An example user control interface 200 for controller unit 130 is illustrated in FIG. 2. The user control interface 200 includes more icons 210, such as an intensity icon 210A, a diagnostic icon 210B, a mode icon 210C and a settings icon 210D, with which user 170 can use for interacting with the FES system 102. It will be understood that the user control interface 200 may include more or fewer icons than shown in FIG. 2, and that the icons may be different from those shown in FIG. 2.

When the controller unit 130 receives a user input activating the intensity icon 210A, the controller unit 130 may allow the user 170 to vary an intensity level of the stimulation signal. Similarly, when the controller unit 130 receives a user input activating the settings icon 210D, the controller unit 130 may allow the user 170 to alter certain operational conditions of the FES system 102. The operational conditions that may be altered may vary based on user type. For example, the user 170 may be limited to cosmetic changes to the user control interface 200, such as background colour, but a doctor or clinician with access to the user control interface 200 may have increased access, such as to alter signal parameters.

In response to receiving a user input activating the mode icon 210C, the controller unit 130 may enable the user 170 to change the operational mode of the FES system 102. Depending on the mode selected by the user 170, the controller unit 130 may vary the signal parameters accordingly.

As described, the FES system 102 may be used for different purposes, such as to facilitate movement of user 170, to reeducate any affected muscles, to retrain the user 170 to walk, or to retard atrophy of muscles due to disuse. Therefore, the FES system 102 may operate in different modes, such as a training mode, a walking mode, a test mode, and a sleep mode. The various different modes may be associated with stimulation signals having different intensity levels and frequencies. It will be understood that fewer or additional number of operational modes may be provided by the controller unit 130 in different embodiments. For example, different stimulation signal parameters may be associated with one or more of the operational modes.

The training mode may be used for reeducating affected muscles or to retard atrophy of muscles while the user 170 is sitting or lying down. The training mode may therefore be associated with stimulation signals with different intensities and different frequencies. The training mode may also be used for initially fitting the user 170 with the stimulation unit 110.

The walking mode may be used for facilitating movement of the user 170. As a result, the walking mode may be associated with stimulation signals with different intensities and different frequencies in comparison with stimulation signals used for the training mode.

The test mode may be used for conducting functional tests and diagnostics of the FES system 102 in order to identify causes of any errors in the FES system 102. The test mode also may be used for calibration, or to carry out a manufacturing procedure or a repair procedure. The test mode will set the FES system 100 into a test mode which one can test and calibrate the FES system parameters. For example, the stimulation unit 110 may be tested to output constant amplitude stimulation signals at certain frequencies for automatically testing certain stimulation signal parameters and calibration procedures.

The sleep mode can help the FES system 102 conserve power. Although each of the stimulation unit 110, the sensor unit 120 and the controller unit 130 may be equipped with a power supply, such as rechargeable lithium-ion batteries for example, power saving can be important for extending a battery life of the FES system 102. Various different power states, such as a power down state, a low power state and an energy saving state may be used. For example, when the sleep mode is selected, the controller unit 130 may power down at least one of the stimulation unit 110 and the sensor unit 120, or place one of the stimulation unit 110 and the sensor unit 120 in a low power state or energy saving state.

In another example of when the sleep mode is selected, the controller unit 130 may synchronize a power usage state as between each of the stimulation unit 110, the sensor unit 120 and the controller unit 130. For synchronizing a low power state among the stimulation unit 110, the sensor unit 120 and the controller unit 130, the controller unit 130 may first transmit a low power state signal to the stimulation unit 110 via the system network 150. Once the stimulation unit 110 enters the low power state, the stimulation unit 110 may send a low power state signal to the sensor unit 120. After the sensor unit 120 enters the low power state, the sensor unit 120 may send a low power state signal to the controller unit 130. In response to receiving the low power state signal, the controller unit 130 transitions to a low power state. The power consumption of the FES system 102 during a low power state can be as low as several mW (nominally).

Each of the stimulation unit 110, the sensor unit 120 and the controller unit 130 can exit the sleep mode in response to receipt of an interrupt signal. The interrupt signal may be a user input received by the controller unit 130 for changing the operational mode from sleep mode, a physical movement of the user 170 as detected by the sensor unit 120, such as detection of a pressure change by the force sensor, or a change in resistance or a user input received by the stimulation unit 110.

Still referring to FIG. 2, when the controller unit 130 receives a user input indicating that the diagnostic icon 210B is selected, the controller unit 130 may prepare reports based on data associated with the operation of the FES system 102. The data associated with the operation of the FES system 102 may be stored with at least one of the controller unit 130 and remotely at external system 140.

The reports may be statistical reports or various usage reports. The operation data may include any data received from the sensor unit 120 and external system 140, and any data collected by the controller unit 130, such as error logs, usage logs, previous waveform parameters, and current waveform parameters. The usage logs may include time and date data, length of use, distance covered, speed, location data (e.g., data provided from the Global Positioning System (GPS)) and other related data.

Figure 3B:
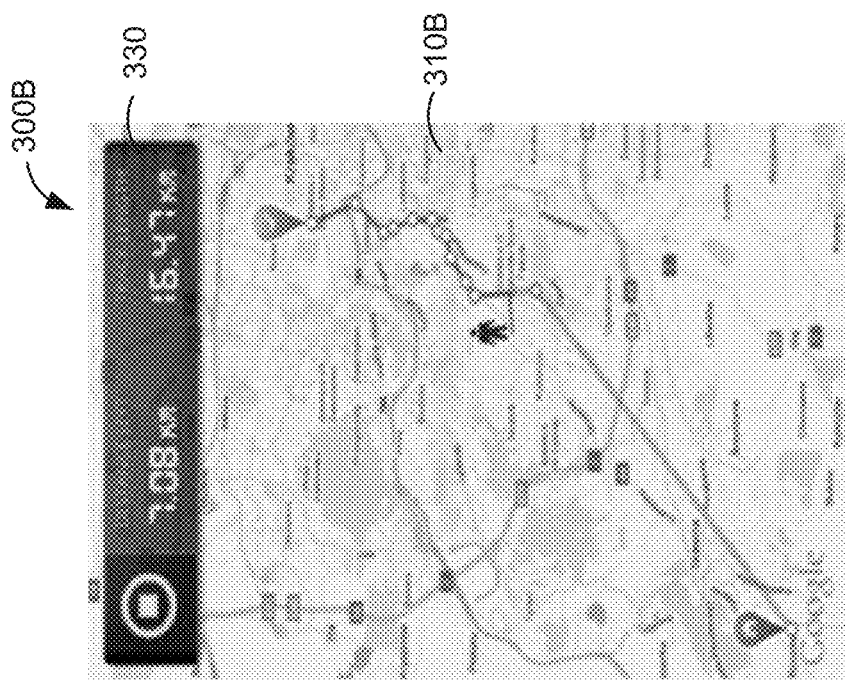
FIGS. 3A and 3B are example screenshots of usage reports generated by the controller unit of the FES system.
Figure 3A:
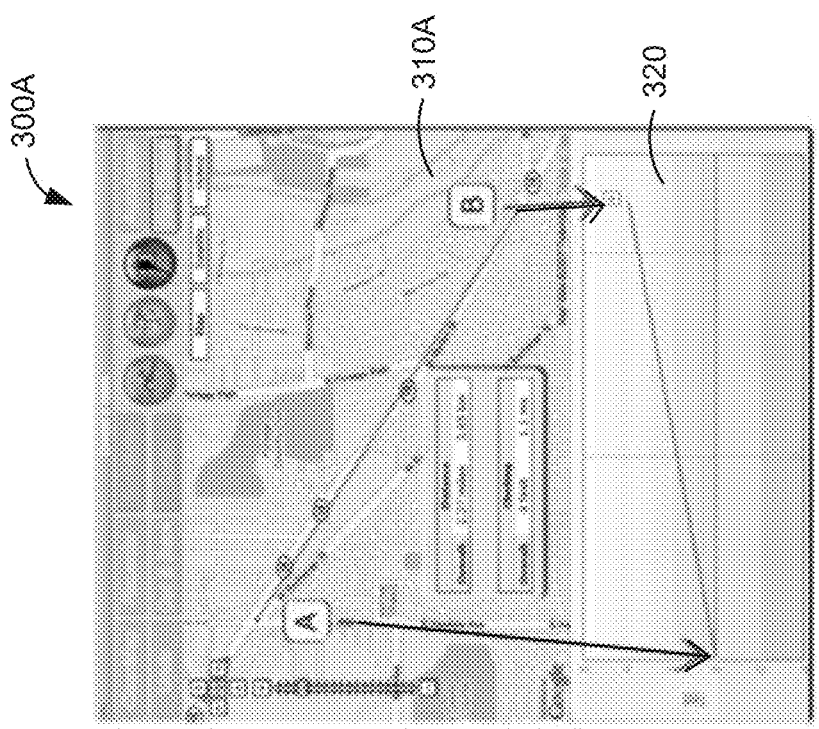

Reference is now made to FIGS. 3A and 3B, which are example usage reports 300A and 300B, respectively, generated by the controller unit 130.

The usage report 300A illustrates a workout performance report. The controller unit 130 may generate a map 310A illustrating a route covered by the user 170 during the workout as well as a graph 320A illustrating a progress of the user 170. The controller unit 130 may additionally provide other performance evaluations, such as the amount of calories burned during the workout. Similarly, the usage report 300B is also a workout performance report. The usage report 300B includes a map 310B of the route of the user 170 and a usage summary 330B. Other reports may be generated that use different colors along the routine 320B to indicate the different speeds of the user 170 during the workout.

The reports generated by the controller unit 130 may be transmitted to the external system 140. Doctors, clinicians or other medical professionals who receive the reports via the external system 140 may review the reports and adjust the signal parameters accordingly.

Referring again to FIG. 1, the external system 140 may include any computing device with at least one processor and memory, and capable of receiving, sending, and processing instructions associated with the operation of the FES system 102. The external system 140 may be directly attached to the FES system 102, via a USB connection, or may connect remotely with the FES system 102 as long as the external system 140 can communicate with the FES system 102 via the public network 160 or the system network 150.

It will be understood that although only one external system 140 is illustrated in FIG. 1, multiple external systems 140 may interact with the FES system 102 at one time. The number of external systems 140 that may interact with the FES system 102 at a given time may be limited by the data transmission capacity of the system network 150 and the public network 160. For example, the FES system 102 will send an alarm to a cell phone, smart phone or other suitable mobile device and at the same time may send a message to a remote computer or a computer that is located in a medical health facility under some circumstances such as when the user 170 falls down or drops to the ground during walking or for emergency situations.

The external system 140 may be an electronic tablet device, a personal computer, a workstation, a server, a portable computer, a mobile device, a personal digital assistant, a laptop, a smart phone, a WAP phone, an interactive television, video display terminals, gaming consoles and portable electronic devices or any combination of these.

Data associated with the usage of the FES system 102 by the user 170 may be transmitted to the external system 140 via the system network 150 or the public network 160. A third party, such as a doctor, clinician or other medical personnel, may access the external system 140 to retrieve the usage data. Based on the usage data, the third party may decide to vary and update certain signal parameters associated with the stimulation signal currently generated by the stimulation unit 110. The external system 140 may then transmit the updated signal parameters to the FES system 102 via the system network 150 or the public network 160.

The external system 140 may also include any device capable of measuring various physiological parameters, such as heart rate and blood oxygen levels. These devices may be worn or carried by the user 170 or attached to at least one unit of the FES system 102. Any physiological information received by the FES system 102 may be analyzed and used for adjusting signal parameters of the stimulation signals. For example, the physiological information may indicate that the heart rate of the user 170 exceeds a recommended heart rate threshold and the FES system 102 may respond by decreasing an intensity of the stimulation signal or disabling the stimulation signal in order to minimize any risk of injury. The physiological information received by the FES system 102 may also be stored at the FES system 102 or at a remote storage system.

The system network 150 includes any network capable of carrying data between each of the stimulation unit 110, the sensor unit 120 and the controller unit 130, as well as between the FES system 102 and the external system 140. System network 150 may include one or more wireless communication networks, such as Wireless LAN (WLAN), a local area network implemented by using technologies such as, but not limited to Bluetooth™ technology or may be infrared light in certain circumstances, and other networks implemented using similar protocols and technologies. The system network 150 may also include multiple sub-networks.

Networks implemented using Bluetooth technologies may be Personal Area Networks (PAN) and can provide enhanced security in comparison with other wireless networks. It is well known that a Bluetooth communication network is capable of exchanging data between different devices over short distances using short-wavelength radio transmissions in the ISM radio band of 2,400 to 2,480 MHz.

Due to the multiple different units within the FES system 102 that may be required to communicate with each other, the FES system 102 may require multi-point connections. When the system network 150 is implemented with Bluetooth technology, the system network 150 may facilitate multi-point connections by entering a special command mode in which two different protocols are used. The two different protocols include the standard Bluetooth communication protocol and an FES system protocol that converts data provided in the standard Bluetooth communication protocol into data recognizable by each of the different units within the FES system 102.

In a command mode, any data received by system network 150 is first interpreted based on the standard Bluetooth communication protocol. Based on the standard Bluetooth communication protocol, the received data is processed and encapsulated with extra bytes in order to match data traditionally provided in the command mode. The processed data can then be interpreted using the FES system protocol.

In embodiments in which the system network 150 is implemented using Bluetooth technology, the FES system 102 may operate to minimize errors in data transmission due to various environment factors. For example, the FES system protocol may introduce a call-respond mechanism to ensure communication reliability with the system network 150.

The public network 160 can include any network capable of carrying data between the external system 140 and the FES system 102. Generally, the public network 160 may be any communication network that is used as the system network 150. However, unlike the system network 150, the public network 160 may also facilitate communication for the external system 140 when it is outside of the range of system network. For example, the public network 160 may include the Internet, Ethernet, a plain old telephone service (POTS) line, a public switch telephone network (PSTN), an integrated services digital network (ISDN), a digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Figure 4:
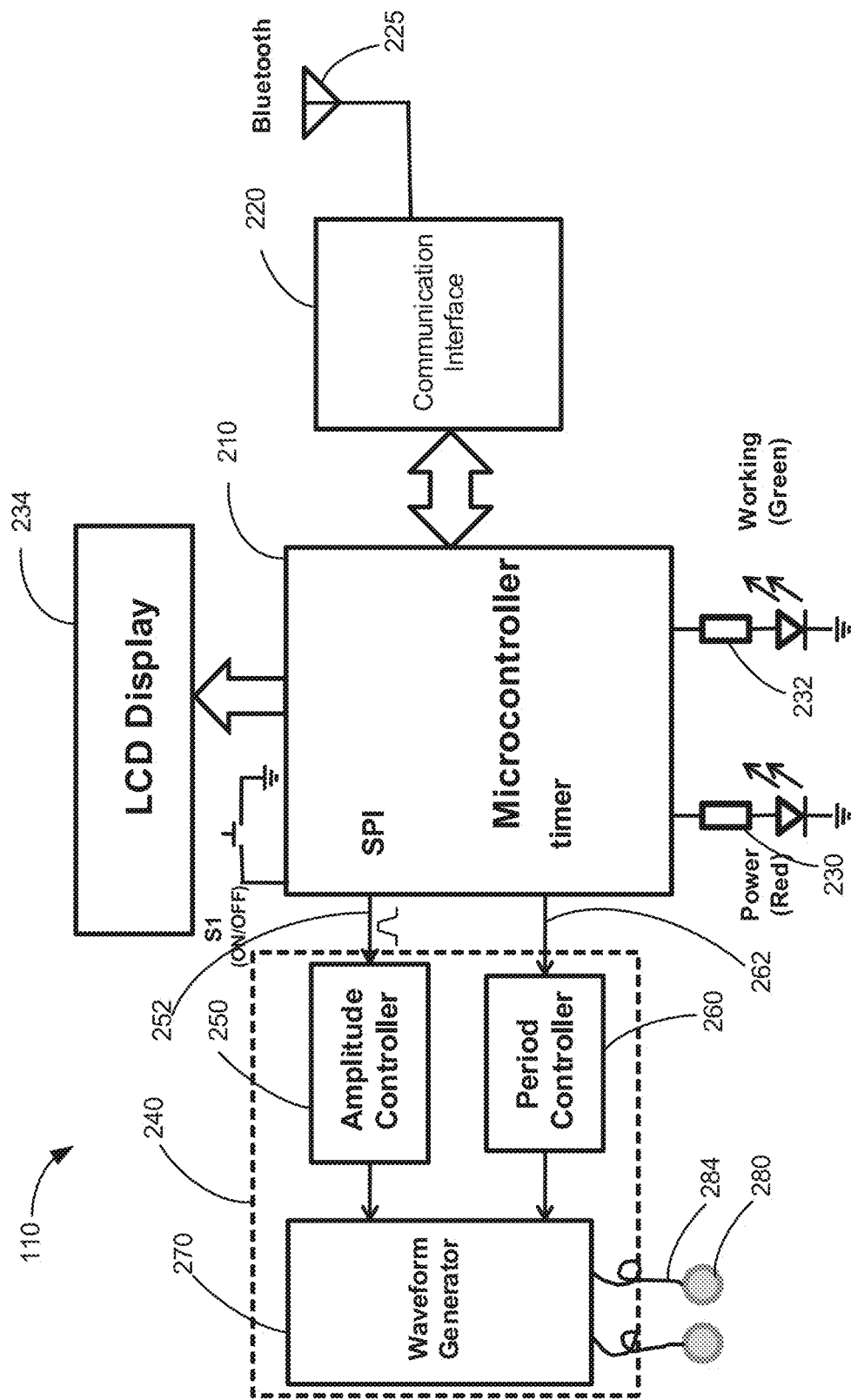
FIG. 4 illustrates a schematic diagram of an example electrical stimulation system.

Referring now to FIG. 4, therein illustrated is a schematic diagram of the stimulation unit 110 according to an example embodiment. The stimulation unit 110 may be provided as an apparatus separate from the sensor unit 120 and the controller unit 130; however the stimulation unit 110 may be in communication with at least one of the sensor unit 120 and the controller unit 130. For example, the stimulation unit 110 may be provided as a flexible printed circuit board (PCB). Use of the flexible PCB in the stimulation unit 110 can offer substantial advantages over conventional PCBs. The flexible PCB is generally lighter than conventional PCBs. Also, the flexible PCB is more malleable and can be bent to accommodate movement of body parts where the stimulation unit 110 is worn by the user.

The stimulation unit 110 includes a microcontroller 210 for receiving and transmitting data signals. The microcontroller 210 may be implemented in hardware or software, or a combination of both. It may be implemented on a programmable processing device, such as a microprocessor or microcontroller, Central Processing Unit (CPU), Digital Signal Processor (DSP), Field Programmable Gate Array (FPGA), general purpose processor, and the like. The programmable processing device is generally coupled to program memory or has its own program memory. The program memory may be used to store instructions used to program the microcontroller 210 to perform various functions as described herein. The program memory can include non-transitory storage media, both volatile and non-volatile, including but not limited to, random access memory (RAM), dynamic random access memory (DRAM), static random access memory (SRAM), read-only memory (ROM), programmable read-only memory (PROM), erasable programmable read-only memory (EPROM), electrically erasable programmable read-only memory (EEPROM), flash memory, magnetic media, and optical media. For example the microcontroller may be a PIC24 series microcontroller.

The microcontroller 210 is coupled to a communication interface 220, which has an antenna 225 for receiving and transmitting wireless signals. The connection with the communication interface 220 allows the microcontroller 210 to receive data signals from at least one of the sensor unit 120, the controller unit 130, and the external system 140 over the system network 150. The microcontroller 210 is operable to receive over the system network 150 at least one set of stimulation parameters that define characteristics of one or more stimulation signals generated by the stimulation unit 110. The microcontroller 210 is further operable to receive a trigger signal.

In at least some embodiments, stimulation parameters are received at the microcontroller 210 of the stimulation unit 110 in real time. Accordingly, stimulation signals generated by the stimulation unit 110 may be based on real time stimulation parameters. When characteristics of the stimulation signals generated by the stimulation unit 110 are to be modified, different stimulation parameters will be received at the microcontroller 210.

According to one example embodiment, the at least one set of stimulation parameters are received at the microcontroller 210 ahead of time. That is, the at least one set of stimulation parameters can be received prior to the stimulation signals having to be generated by the stimulation unit 110. The at least one set of stimulation parameters that are received can be stored within the microcontroller 210 to be retrieved at a later time.

For example, the at least one set of stimulation progress can be downloaded over the system network 150 from either the external system 140 or the controller unit 130.

In another example, based on physiological changes of a user, a doctor may wish to adjust stimulation signals applied to the user. The doctor may do so by submitting updated stimulation parameters from the external system 140 to the stimulation unit 110.

In another example, the microcontroller 210 can receive a plurality of sets of stimulation parameters. One or more sets of the plurality of received stimulation parameters may be associated with a particular operation mode. For example, different sets of stimulation parameters may be associated with each one of the training mode, walking mode, test mode, or sleep mode. Furthermore, within each mode, additional sets of stimulation parameters may be available. For example, different sets of stimulation parameters may be available for selection based on terrain, weather, etc. Accordingly, a set of stimulation parameters may be selected based on the selected operational mode. For example, the microcontroller 210 may receive from one of the sensor unit 120, the controller unit 130 or external system 140 a mode signal indicating an active operational mode, which further indicates a particular set of stimulation parameters to be selected. This allows stimulation signals generated by the stimulation unit 110 to be varied according to the selected operational mode.

Different sets of stimulation parameters may also be associated with different values of the various sensors provided by the sensor unit 120. For example different stimulation parameters may be associated with varying amounts of force received by the force sensor, varying temperatures detected by the temperature sensor, varying orientation data from the sensor unit 120 indicating a change in the position of the user, varying accelerations detected by the accelerometer, or a varying magnetic field detected by the compass. Accordingly, a set of stimulation parameters may be selected based on one type of sensor data or a combination of various sensor data.

According to various example embodiments, the stimulation unit 110 may include a display device 234. For example the display device 234 can be a liquid crystal display as indicated in the example shown in FIG. 4. The display device 234 is coupled to the microcontroller 210 and receives data therefrom. The display device 234 can be used to display information related to the status of the stimulation unit 110. For example the display device 234 can display one or more of a currently selected operation mode, an identifier of the selected set of stimulation parameters, or the fact that a suitable set of stimulation parameters is not available.

According to various example embodiments, the stimulation unit 110 may include one or more indicator lights 230, 232. For example the one or more indicator lights 230, 232 may be light emitting diodes that emit different colors. The one or more indicator lights 230, 232 are coupled to the microcontroller 210 and receive data therefrom. The lights 230, 232 can be used to display information related to the status of the stimulation unit 110. For example, the red light 230 may be turned on to indicate that the stimulation unit 110 is powered on and the green light 232 may be turned onto indicate that the stimulation unit 110 is currently operating to generate stimulation signals.

The stimulation unit 110 includes a signal generation submodule 240 coupled to the microcontroller 210 for generating one or more stimulation signals to be delivered to the user 170. Based on the at least one set of stimulation parameters, the microcontroller 210 outputs a plurality of stimulation control signals for controlling the signal generation submodule 240. The plurality of control signals are received by the signal generation submodule 240. The signal generation submodule 240 includes an amplitude controller unit 250, a controller unit 260 and a waveform generator 270. The waveform generator 270 is then further coupled to contact electrodes 280 that are part of the cuff 180. The contact electrodes 280 are generally positioned to contact an area of the user 170 that is to be stimulated. Stimulation signals generated by the waveform generator 270 are outputted via a stimulation channel output 284 to the contact electrodes 280 for stimulating a body part of the user 170.

According to various example embodiments, the stimulation unit 110 can include a plurality of signal generation submodules 240. For example, a given signal generation submodule 240 may be provided for each of the stimulation channels available at the stimulation unit 110. Each of the stimulation submodules 240 may generate one of the stimulation signals over one of the channels. For example, the plurality of signal generation submodules 240 can be controlled by the microcontroller 210.

The values of the control signals outputted by the microcontroller 210 correspond to values of the selected set of stimulation parameters. That is, the values of the control signals outputted by the microcontroller 210 are adjusted based on values of the selected set of stimulation parameters. According to various example embodiments, the stimulation parameters define the value of the control signals sent to the signal generation submodule 240.

The values of the control signals outputted by the microcontroller 210 can also be adjusted based on stimulation parameter values that are calculated on-the-fly. For example, data from the sensor unit 120 may be received at the microcontroller 210 via the communication interface 220. The data from the sensor unit 120 is then analyzed and stimulation parameters are calculated based on the analysis. Values of the control signals corresponding to the calculated stimulation parameters are then sent to the signal generation submodule 240.

Alternatively, the stimulation parameters define characteristics of the stimulation signals that are to be generated. In this case, the microcontroller 210 may have a stored waveform data chart (an example of which is shown in Table 1) that define values of the control signals that are to be sent to the signal generation submodule 240 such that when the elements of the signal generation submodule 240 are controlled according to the control signals, the generated stimulation signals will have the characteristics defined by the waveform parameters. The waveform data chart may be compiled based on specifications of one or more elements of the signal generation submodule 240. For example, different models of the stimulation unit 110 can have different specifications, such as size of the stimulation unit 110, power output, output channel number, or battery capacity. Using a stored waveform data chart that is compiled according to the specifications of the signal generation submodule 240 allows stimulation parameters to be defined independently of the specifications of the stimulation unit 110. For example, a doctor can apply a particular set of stimulation parameters to multiple patients who are wearing stimulation units 110 having different specifications. The use of a stored waveform data chart ensures that the same stimulation signals generated based on the particular set of stimulation parameters are applied to each of the patients despite the patients using differently specified stimulation units 110.

According to various example embodiments, the microcontroller 210 outputs the control signals in response to the received trigger signal. For example, the trigger signal may indicate when control signals should be output to generate stimulation signals for stimulating a body part of the user 170 or when control signals should not be outputted so that the user 170 is not stimulated. For example, a trigger signal may be sent from the sensor unit 120. The trigger signal may be generated based on a change in position of the user 170 sensed by the sensor unit 120. It will be appreciated that in some positions (for example, a resting position), the user 170 does not require stimulation of the body part, while in other positions (ex: standing, moving), the user 170 benefits from stimulation of the body part.

Figure 5A:
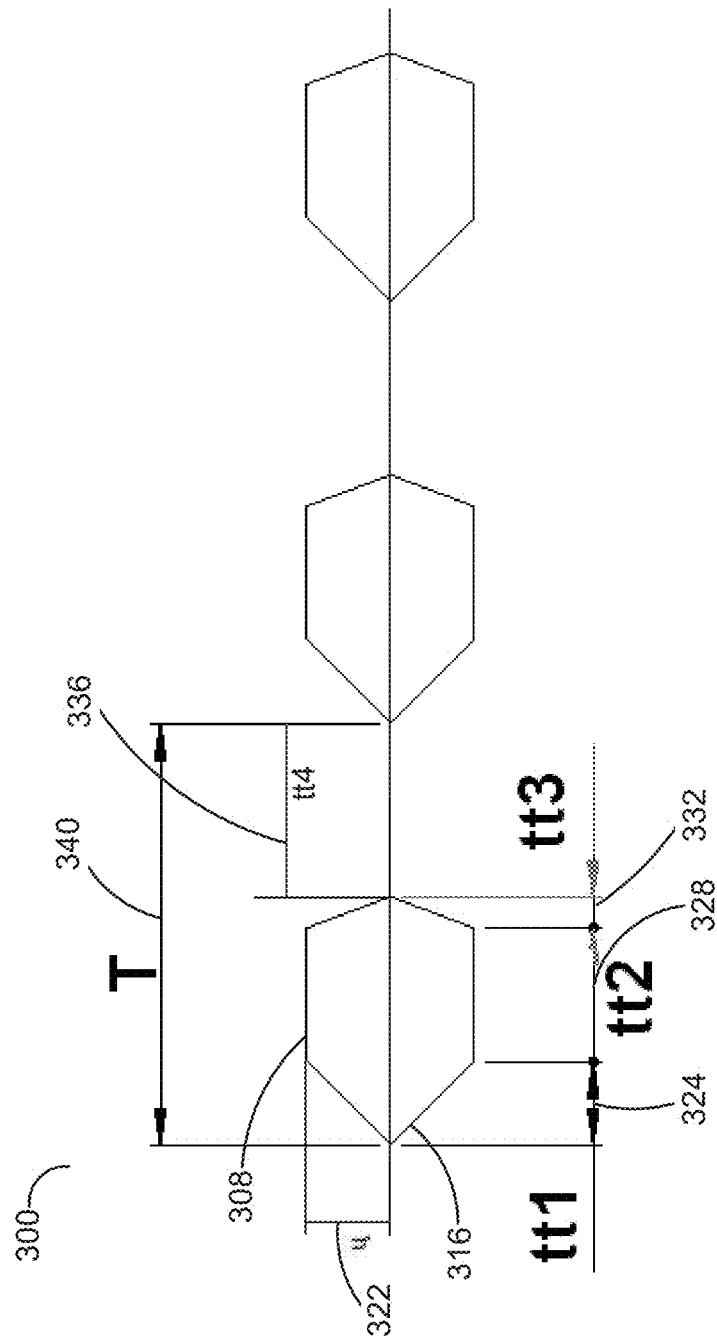
FIG. 5A illustrates an amplitude waveform according to an example embodiment.

Referring now to FIG. 5A, therein illustrated is a waveform 300 of an amplitude portion of an example stimulation signal that is generated by the stimulation unit 110. As shown in FIG. 5A, a positive amplitude waveform 308 and a negative amplitude waveform 316 are shown simultaneously and superimposed. It will be understood that the positive amplitude waveform 308 and the negative amplitude waveform 316 corresponds to an intermediate signal generated within the signal generation submodule 240.

According to various example embodiments, the amplitude controller 250 receives at least a first control signal 252 of the control signals outputted by the microcontroller 210 and controls the waveform generator 270 such that at least one of the positive amplitude waveform 308 and the negative amplitude waveform 316 is generated. The positive amplitude waveform 308 and negative amplitude waveform 316 represent intermediate signals in the generation of stimulation signals. The first control signal 252 corresponds to a desired amplitude of the stimulation signal to be outputted. The desired amplitude can be indicated within the selected set of stimulation parameters. For example, the value of the first control signal 252 is determined by referencing the waveform data chart and finding the defined value of the first control signal for generating a stimulation signal having the given desired amplitude.

For example, the first control signal 252 may be a time varying signal corresponding to desired amplitude values over time. The desired amplitude values over time may be indicated within the selected set of stimulation parameters.

Alternatively where the stimulation signal is to be repeated more than once, the selected set of stimulation parameters can define characteristics of a cycle of the stimulation signal. For example, the stimulation parameters can define a desired amplitude u 322, a rise time tt1 324, a hold time tt2 328, a fall time tt3 332, and an idle time tt4 336. The rise time tt1 324 of the stimulation signal corresponds to when the amplitude value rises from a reference value (e.g., 0V) to the desired amplitude value u 322. The hold time tt2 328 of the stimulation signal corresponds to how long the desired amplitude is maintained. The fall time tt3 332 corresponds to when the amplitude value falls from the desired amplitude value back to the reference value. The idle time tt4 336 corresponds to how long the stimulation signal is maintained at the reference value before the start of another stimulation cycle. The entire duration of the stimulation cycle has a time T 340.

According to one example embodiment, the selected set of stimulation parameters only defines the positive portion of the desired amplitude values, and a corresponding negative waveform is simply the negative of the positive waveform. That is, the negative waveform is symmetric with the positive waveform about the reference value.

Figure 5B:
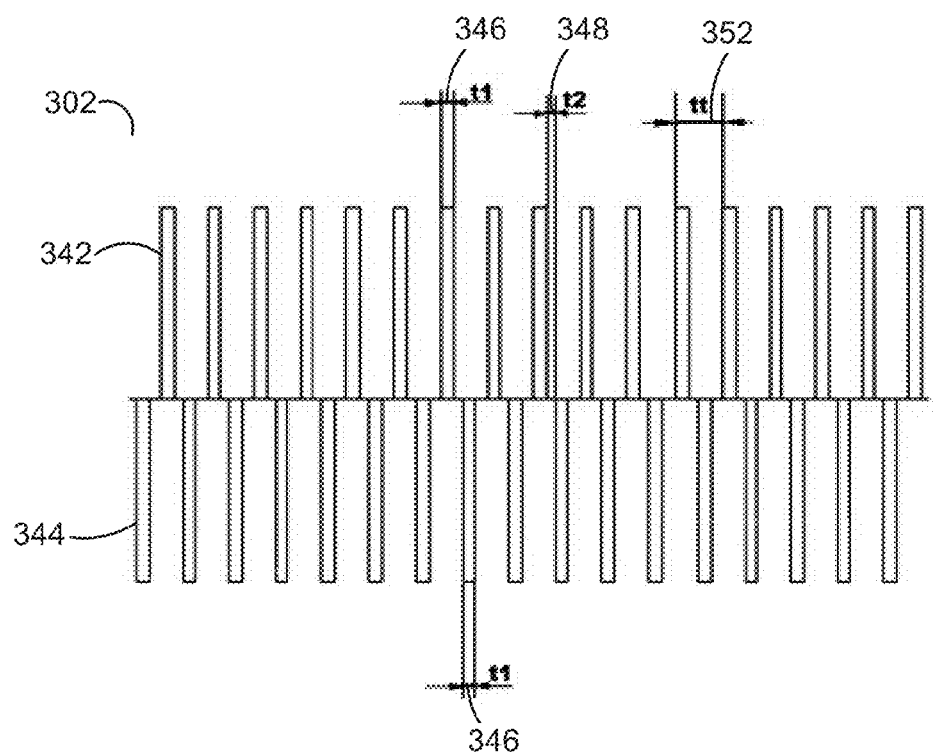
FIG. 5B illustrates a pulse waveform according to an example embodiment.

Referring now to FIG. 5B, therein illustrated is a waveform 302 of a pulsed portion of an example stimulation signal that is generated by the stimulation unit 110. As shown in FIG. 5B, a positive pulse signal 342 and a negative pulse signal 344 are shown simultaneously and superimposed. According to one example embodiment, the positive pulse signal 342 and the negative pulse signal 344 are generated separately. It will be understood that the positive pulse signal 342 and the negative pulse signal 344 correspond to intermediate signals generated within the signal generation submodule 240. For example, a second control signal 262 may be used which is a time varying signal defining output values over time.

The selected set of stimulation parameters can define a duration of a pulse (i.e. desired pulse width) and an interval between two adjacent pulses (i.e. period of the pulse). For example, the stimulation parameters may define the duration of a positive pulse and interval between two adjacent positive pulses and also the duration of a negative pulse and the interval between two adjacent negative pulses. The stimulation parameters may further define an offset (i.e. phase) between the positive pulses and the negative pulses.

According to one example embodiment, the desired positive pulse signal and the desired negative pulse signal may be defined together. For example the stimulation parameters may define duration t1 346, duration t2 348, and duration tt 352. The duration t1 346 defines the duration of a non-zero positive pulse of the positive pulse signal 342 (i.e. desired pulse width). In some example embodiments, the duration t1 346 also defines the duration of a non-zero negative pulse of the negative pulse signal 344. However, in some example embodiments, different parameters (such as t1 p and t1n) may be used with different values when the duration (t1p) of the non-zero positive pulse and the duration (t1n) of the non-zero negative pulse are not equal. The duration t2 348 defines the duration of the interval between the end of a positive pulse and the start of the next negative pulse. The duration tt 352 defines the duration of the interval between the start of two adjacent positive pulses, which may also correspond to the duration of the interval between the start of two adjacent negative pulses (i.e. desired period). It will be appreciated that the manner of defining the positive and negative pulse signals 342 and 344 are described for example purposes only and that other ways of defining the positive and negative pulse signals 342 and 344 may also be used in other embodiments.

For example, the second control signal 262 may be used to define the start times and stop times of the positive amplitude waveform 308 and the start times and stop times of the negative amplitude waveform 316. These output values may be indicated within the selected set of stimulation parameters.

According to various example embodiments, the period controller 260 receives at least a second control signal 262 of the control signals outputted by the microcontroller 210 and controls the waveform generator 270 based on the second control signal 262. The waveform generator 270 is controlled so that the generated positive and negative amplitude waveforms 308 and 316 of FIG. 5A is outputted as the stimulation signal based on one or both of the negative and positive pulse signals 342 and 344. For example, the positive amplitude waveform 308 is outputted as the stimulation signal at durations of time corresponding to when the positive pulse signal 342 has a non-zero value and the negative amplitude waveform 316 is outputted as the stimulation signal at durations of time corresponding to when the negative pulse signal 344 has a non-zero value. According to at least some embodiments, the positive pulse signal 342 and the negative pulse signal 344 cannot simultaneously have non-zero values, as such a signal may be damaging to the device, for the safety of the user 170.

Figure 5C:
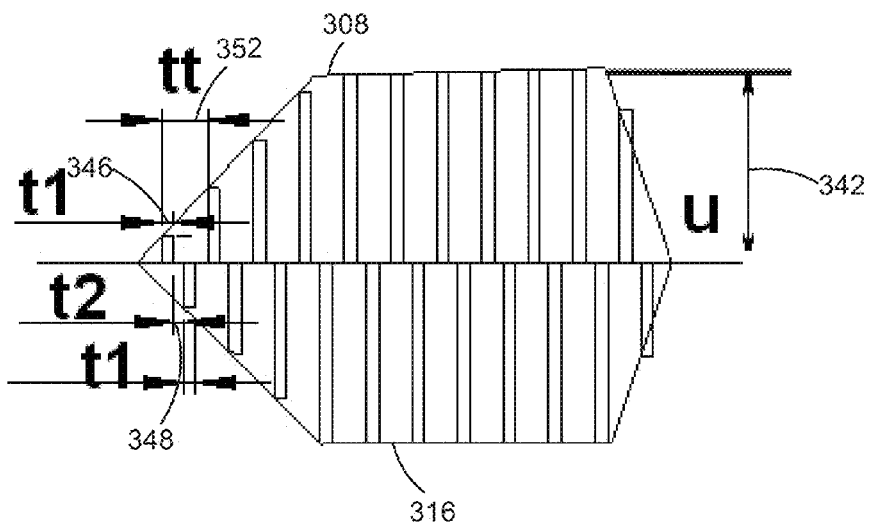
FIG. 5C illustrates a combination of the amplitude waveform and the pulse waveform according to an example embodiment.

Referring now to FIG. 5C, therein illustrated is a combination of the waveform 300 and waveform 302 of an example stimulation signal that is generated by the stimulation unit 110. An overlap in time of a non-zero positive pulse signal 342 with a non-zero positive amplitude waveform 308 represents when the positive waveform 308 is outputted as the stimulation signal. An overlap in time of a non-zero negative pulse signal 344 with a non-zero negative amplitude waveform 316 represents when the negative waveform 316 is outputted as the stimulation signal.

Figure 5D:
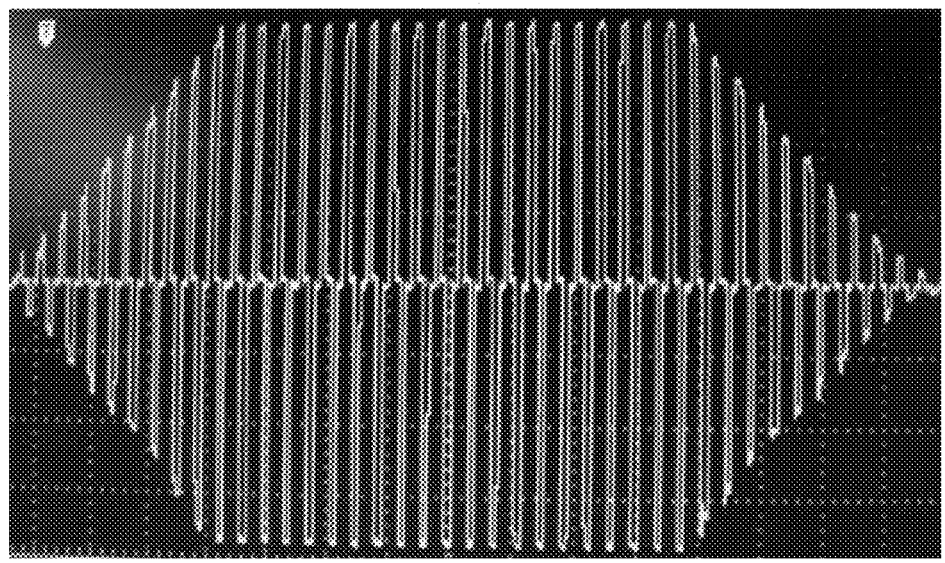
FIG. 5D illustrates an example stimulation signal that is outputted according to an example embodiment.

Referring now to FIG. 5D, therein illustrated is an example stimulation signal 360 outputted from the waveform generator 270. Due to controlling of the amplitude waveforms 308 and 316 according to one or both of the negative and positive pulse signals 342 and 344, the generated stimulation signals appears as a pulsed signal having a time varying amplitude. The variation of the amplitude is defined by the positive and negative amplitude waveforms 308 and 316. Whether the positive waveform 308, negative waveform 316, or reference value is outputted is defined by the non-zero pulses of the positive pulse signal 342 and negative pulse signal 344. It will be appreciated that the generated stimulation signal 360 resembles an amplitude modulated signal wherein the amplitude waveform 300 is the envelope wave and the pulsed signals 302 acts as the carrier wave.

Figure 6:
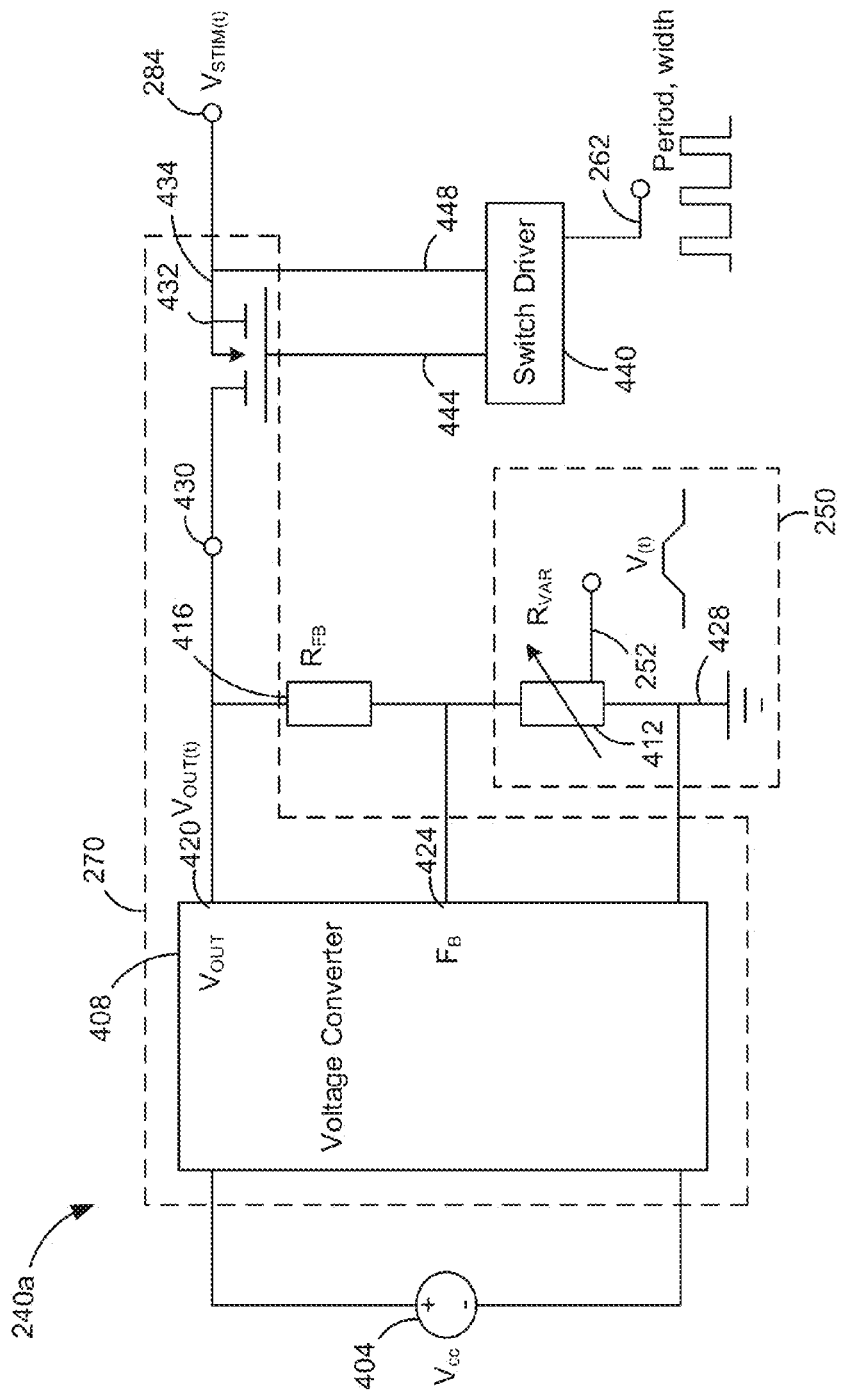
FIG. 6 illustrates a schematic circuit diagram of a sub-module of the electrical stimulation system according to an example embodiment.

Referring now to FIG. 6, therein illustrated is a circuit diagram of a portion of an example signal generation submodule 240a according to an example embodiment. The signal generation submodule 240a includes a voltage supply 404 that provides voltage to a voltage converter module 408 coupled to the voltage supply 404. The voltage converter module 408 receives the first control signal 252 of the simulation control signals and converts the voltage received from the voltage supply 404 based on the value of the first control signal 252. The signal generation module 240a may be used in situations where it is required to provide a stimulation signal that only has one polarity.

According to this example embodiment, the voltage converter module 408 includes a DC/DC Boost voltage converter 408 and a variable resistor 412. A feedback resistor 416 couples a voltage output terminal 420 of the DC/DC voltage converter 408 to a feedback terminal 424 of the DC/DC voltage converter 408. The variable resistor 412 further couples the feedback terminal 424 to a reference 428, such as ground. Due to the voltage output terminal 420 being coupled to the feedback terminal 424, the value of the converted voltage outputted from the voltage output terminal 420 can be greater than the voltage from the voltage supply 404. The converted voltage is based on the resistance value $R_{FB}$ of the feedback resistance 416 and the resistance value $R_{var}$ of the variable resistance 412. The converted voltage 420 may be based on a ratio of the resistance value of the feedback resistance 416 and the resistance value of the variable resistance 412. For example, the converted voltage may be calculated according to equation 1.

$$V_{out} = V_{in}\left(1 + \frac{R_{FB}}{R_{Var}}\right) \quad (1)$$

According to at least one embodiment, the first control signal 252 is a time varying signal and the value $R_{var}$ of the variable resistance 412 is varied in time according to the first signal 252. Accordingly the converted voltage outputted at output terminal 420 also varies in time to form a waveform with a time-varying amplitude. As shown in FIG. 6, one of the positive amplitude waveform 308 or the negative amplitude waveform 316 can be outputted from the voltage conversion module.

According to at least one embodiment, the variable resistor 412 may be implemented as part of a digital potentiometer. The digital potentiometer 412 receives the first control signal 252 from the microcontroller 210. In this case the first control signal 252 can be a digital signal.

Since the converted voltage outputted from the output terminal 420 is based on the resistance value $R_{var}$ of the variable resistor 412, the first control signal 252 is used to define values of the resistance $R_{var}$ that is to be set. The microcontroller 210 outputs a given resistance value $R_{var}$ in the first control signal 252 based on a desired amplitude value of the stimulation signal to be generated. For example, for a given desired amplitude value that is defined in the stimulation parameters, the microcontroller 210 can retrieve, from the waveform data chart, a corresponding resistance value $R_{var}$ for adjusting the variable resistor 412. Adjusting the variable resistor 412 to have the resistance value $R_{var}$ results in the converted voltage outputted from output terminal 420 to have approximately the desired amplitude value. For example, for a range of desired amplitude values of the stimulation signal that is to be generated, the corresponding resistance values $R_{var}$ of the variable resistor 412 can be predetermined and stored in the waveform data chart. For example, determination of the resistance values $R_{var}$ corresponding to different desired amplitude values of the stimulation signal can be made when designing or configuring the stimulation unit 110.

Referring now to Table 1, therein illustrated is an example waveform data chart showing resistance values $R_{var}$ (in kΩ) for different values $R_{FB}$ (in kΩ) of the feedback resistor 416 and different desired voltage amplitude values. Resistance values $R_{var}$ may be determined according to the equation $$V_{out} = V_{in}\left(1 + \frac{R_{FB}}{R_{Var}}\right)$$

for this example embodiment.

Controlling of the switch 432 between its open position and its closed position provides selective control of whether the converted voltage of the output terminal 420 is outputted at the stimulation channel output 284. When a positive or negative amplitude waveform is outputted at the output terminal 420 of the voltage converter 408, controlling of the switch 432 controls whether the amplitude waveform is outputted as the generated stimulation signal. Closing the switch 432 outputs the amplitude waveform as the generated stimulation signal. Opening the switch 432 creates an open circuit, and a reference value (e.g. 0V) signal is outputted as the stimulation signal at the stimulation channel output 284.

The signal generation submodule 240a includes a driver module 440 that is a switch driver for controlling the switch 432 between its open and closed state. The driver module 440 receives the second control signal 262 and controls the switch 432 based on the value of the second signal 262. As described

TABLE 1

An example Waveform Data Chart

| Voltage (V) | $R_{FB}$ = 500K | $R_{FB}$ = 400k | $R_{FB}$ = 300K | $R_{FB}$ = 200K | $R_{FB}$ = 100K | $R_{FB}$ = 90K | $R_{FB}$ = 80k | $R_{FB}$ = 70K | $R_{FB}$ = 47K |
|---|---|---|---|---|---|---|---|---|---|
| 2 | 833.3333 | 666.6667 | 500 | 333.3333 | 166.6667 | 150 | 133.3333 | 116.6667 | 78.33333 |
| 3 | 357.1429 | 285.7143 | 214.2857 | 142.8571 | 71.42857 | 64.28571 | 57.14286 | 50 | 33.57143 |
| 4 | 227.2727 | 181.8182 | 136.3636 | 90.90909 | 45.45455 | 40.90909 | 36.36364 | 31.81818 | 21.36364 |
| 5 | 166.6667 | 133.3333 | 100 | 66.66667 | 33.33333 | 30 | 26.66667 | 23.33333 | 15.66667 |
| 6 | 131.5789 | 105.2632 | 78.94737 | 52.63158 | 26.31579 | 23.68421 | 21.05263 | 18.42105 | 12.36842 |
| 7 | 108.6957 | 86.95652 | 65.21739 | 43.47826 | 21.73913 | 19.56522 | 17.3913 | 15.21739 | 10.21739 |
| 8 | 92.59259 | 74.07407 | 55.55556 | 37.03704 | 18.51852 | 16.66667 | 14.81481 | 12.96296 | 8.703704 |
| 9 | 80.64516 | 64.51613 | 48.3871 | 32.25806 | 16.12903 | 14.51613 | 12.90323 | 11.29032 | 7.580645 |
| 10 | 71.42857 | 57.14286 | 42.85714 | 28.57143 | 14.28571 | 12.85714 | 11.42857 | 10 | 6.714286 |
| 11 | 64.10256 | 51.28205 | 38.46154 | 25.64103 | 12.82051 | 11.53846 | 10.25641 | 8.974359 | 6.025641 |
| 12 | 58.13953 | 46.51163 | 34.88372 | 23.25581 | 11.62791 | 10.46512 | 9.302326 | 8.139535 | 5.465116 |
| 13 | 53.19149 | 42.55319 | 31.91489 | 21.2766 | 10.6383 | 9.574468 | 8.510638 | 7.446809 | 5 |
| 14 | 49.01961 | 39.21569 | 29.41176 | 19.60784 | 9.803922 | 8.823529 | 7.843137 | 6.862745 | 4.607843 |
| 15 | 45.45455 | 36.36364 | 27.27273 | 18.18182 | 9.090909 | 8.181818 | 7.272727 | 6.363636 | 4.272727 |
| 16 | 42.37288 | 33.89831 | 25.42373 | 16.94915 | 8.474576 | 7.627119 | 6.779661 | 5.932203 | 3.983051 |
| 17 | 39.68254 | 31.74603 | 23.80952 | 15.87302 | 7.936508 | 7.142857 | 6.349206 | 5.555556 | 3.730159 |
| 18 | 37.31343 | 29.85075 | 22.38806 | 14.92537 | 7.462687 | 6.716418 | 5.970149 | 5.223881 | 3.507463 |
| 19 | 35.21127 | 28.16901 | 21.12676 | 14.08451 | 7.042254 | 6.338028 | 5.633803 | 4.929577 | 3.309859 |
| 20 | 33.33333 | 26.66667 | 20 | 13.33333 | 6.666667 | 6 | 5.333333 | 4.666667 | 3.133333 |

When designing the voltage conversion module 408, the resistance value $R_{FB}$ of the feedback resistor 416 may be selected based on an expected range of voltage amplitudes, the voltage of the power supply 404, the range of positive resistance values of available variable resistor 412 and the resolution of the variable resistor 412. For example, a 100 kΩ feedback resistor 416 is optimal for achieving voltage amplitudes in an amplitude range of 2V to 20V from a power supply supplying 3.3V and for a variable resistor having a range of possible resistance values between 0Ω and 200 kΩ. According to this configuration, if the stimulation parameters define a desired voltage amplitude of 15 V, the first control signal 252 will include a resistance value $R_{var}$ of 9.090909 kΩ for adjusting the variable resistor 412.

It will be appreciated that adjusting of the resistance value $R_{var}$ of the variable resistor 412 results in an adjusting of the converted voltage 420. Accordingly the amplitude controller 250 of the signal generation submodule 240a can be implemented using the variable resistor 412.

Continuing with FIG. 6, the output terminal 420 of the voltage converter module 408 is coupled to a first terminal 430 of a switch 432. The second terminal 434 of the switch is coupled to a submodule output 284 of the signal generation submodule 240a, which outputs the generated stimulation signal. For example, the output 284 is coupled to the contact electrodes 280.

above, the second signal 262 can be a pulsed wave. Accordingly, the driver module 440 controls the switch 432 to move to the closed position during a time interval corresponding to a nonzero (i.e. positive or negative) pulse. The driver module 440 controls the switch 432 to move to the open position during time intervals corresponding to when there is no pulse (i.e. the pulse value is zero). It will be appreciated that controlling the switch 432 in this manner results in the converted voltage from the output terminal 420 being outputted as the stimulation signal at the stimulation channel output 284 only at time intervals corresponding to a non-zero pulse in the pulse signal. As shown in FIG. 6, since only one of the positive amplitude waveform 308 or the negative amplitude waveform 316 can be outputted from the voltage conversion module 408, the switch 432 is operable to output only one of the amplitude waveforms 308, 316 as the stimulation signal at stimulation channel output 284.

In at least some embodiments, the switch 432 is a MOSFET switch and the switch driver module 440 includes a MOSFET driver. As shown in FIG. 6, a first intermediate control signal 444 from the driver module 440 is coupled to a gate terminal of the MOSFET switch 432 and a second intermediate control signal 448 is coupled to a source terminal of the MOSFET switch 432. Advantageously, use of a MOSFET switch and a MOSFET driver provide for fast switching, increased power efficiency and lower power consumption.

It will be appreciated that control signals from the switch driver module 440 based on the received second control signal 262 results in a control of when the amplitude waveform is outputted as the stimulation signal. Accordingly the period controller 260 of the signal generation submodule 240a can be implemented using the driver module 440.

According to the example embodiment shown in FIG. 6, the voltage converter is provided with only one voltage output 420 and only one switch. Therefore only one of the positive amplitude waveform or the negative amplitude waveform may be formed by the voltage converter module 408. Also only one of the positive pulse signal 342 or the negative pulse signal 344 is received as the second control signal 262 at the driver module 440. As a result, the stimulation signal that is outputted has only a positive component or a negative component.

Figure 7A:
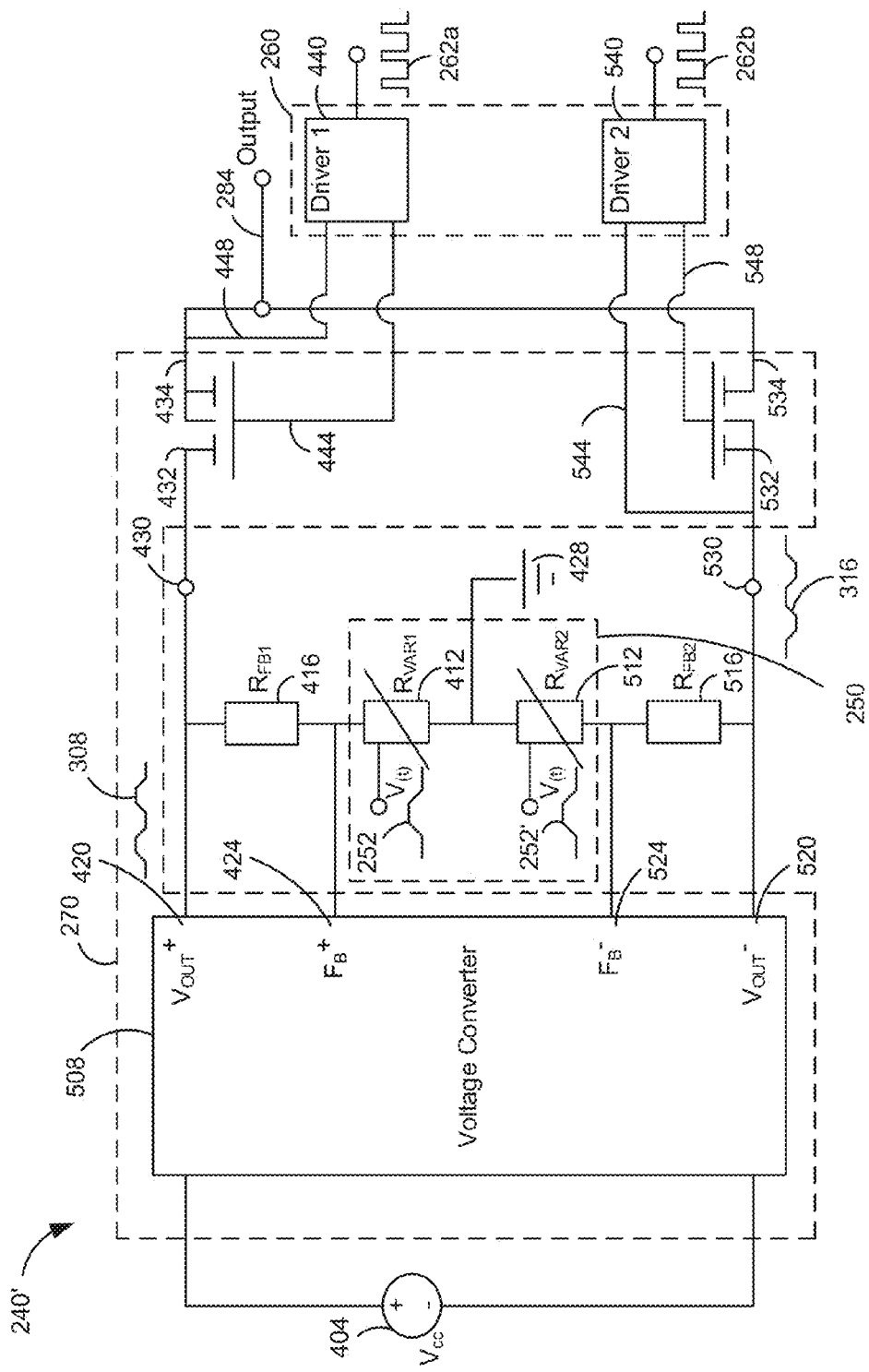
FIG. 7A illustrates a schematic circuit diagram of a sub-module of the electrical stimulation system according to an example embodiment.

Referring now to FIG. 7A, therein illustrated is a schematic diagram of an example signal generation submodule 240' capable of generating a stimulation signal having both a positive and a negative component. It will be appreciated that the embodiment of FIG. 7A resembles portions of the example signal generation submodule 240 shown in FIG. 6 and has several elements repeated.

A voltage converter 508 is coupled to the voltage supply 404. A first feedback terminal resistor 416 couples a positive voltage terminal 420 of an upper portion of the voltage convertor 508 to a first feedback terminal 424 of the voltage converter 408. A first variable resistor 412 further couples the first feedback terminal 424 to a reference voltage 428. The converted voltage outputted from the positive voltage terminal 420 corresponds to the positive amplitude signal 308. The voltage converter 508 further includes a lower portion. A second feedback resistor 516 couples a negative voltage terminal 520 of the lower portion of the voltage converter 508 to a second feedback terminal 524 of the lower portion. A second variable resistor 512 further couples the second feedback terminal 524 to the reference voltage 428. The converted voltage outputted from the negative voltage terminal 520 corresponds to the negative amplitude signal 316.

As shown in FIG. 7A, the upper and lower portions are implemented within a single dual-boost DC/DC converter 508 operable to convert the supply voltage 404 and output two converted voltages. The value of the first converted voltage $V_{out}^+$ outputted at the first output terminal 420 is based on the resistance value $R_{FB1}$ of the first feedback resistor 416 and the resistance value $R_{var1}$ of the first variable resistance. The value of the second converted voltage $V_{out}^-$ outputted at the second output terminal 520 is based on the resistance value $R_{FB2}$ of the second feedback resistor 516 and the resistance value $R_{var2}$ of the second variable resistance 512. For example, according to a suitably designed dual DC/DC voltage converter, the first converted voltage $V_{out}^+$ and the second converted voltage $V_{out}^-$ can be computed according to equations 2 and 3.

$$V_{out}^+ = V_{in}\left(1 + \frac{R_{FB1}}{R_{Var1}}\right) \quad (2)$$

$$V_{out}^- = -V_{in}\left(\frac{R_{FB2}}{R_{Var2}}\right) \quad (3)$$

In at least some embodiments, the first variable resistor 412 and the second variable resistor 512 may be implemented as part of a dual digital potentiometer. The dual potentiometer receives the first control signal 252 from the microcontroller 210. In this case the first control signal 252 can be a digital signal.

Furthermore, the first control signal 252 may include at least two components. For example, the two components may be sent as separate control signals. A first component of the first control signal 252 indicates a resistance value $R_{var1}$ for adjusting the first variable resistor 412 so that the converted voltage outputted at the first output terminal 420 has the desired positive amplitude value defined in the selected set of stimulation parameters. A second component of the first control signal 252 indicates a resistance value $R_{var2}$ for adjusting the second variable resistor 512 so that the converted voltage outputted at the second output terminal 520 has the desired negative amplitude value defined in the selected set of stimulation parameters. For example, the values $R_{var1}$ and $R_{var2}$ can be determined according to a waveform data chart stored in the microcontroller 210.

The example signal generation submodule 240' further includes a first switch 432 for selectively outputting the positive amplitude waveform 308 through control of the switch 432 based on the positive pulse signal 342 of the second signal 262 received at the first driver module 440. The example signal generation submodule 240' also includes a second switch 532 for selectively outputting the negative amplitude waveform 316 through control of the second switch 532 based on a negative pulse signal 344 of the second signal 262 received at a second driver module 540. Both the first switch 432 and the second switch 532 may be MOSFET switches and both the first and second switch driver modules 440 and 540 may be MOSFET drivers. In at least some embodiments, the first driver module 440 and the second driver module 540 are implemented as part of a dual isolated MOSFET driver.

As shown in FIG. 7A, the first intermediate control signal 444 from the first driver module 440 is coupled to a gate terminal of the first MOSFET switch 432 and a second intermediate control signal 448 is coupled to a source terminal of the first MOSFET switch 432. A second intermediate control signal 544 from the second driver module 540 is coupled to a gate terminal of the second MOSFET switch 532 and a second intermediate control signal 548 is coupled to a source terminal of the second MOSFET switch 532. Since the negative amplitude waveform 316 is negative, the second output terminal 520 of the converter 508 is coupled to the source terminal of the second MOSFET switch 532.

The second control signal 262 may include at least two components 262a and 262b. For example, the two components may be sent as separate control signals. A first component of the second control signal 262a may include the positive pulse signal 342 for controlling the first switch 432. A second component of the second control signal 262b may include the negative pulse signal 344 for controlling the second switch 532. For example, the microcontroller 512 is enabled to generate the positive pulse signal 342 and the negative pulse signal 344 based on characteristics defined in the selected set of stimulation parameters.

The output terminal 434 of the first switch 432 (the source terminal in the case of a MOSFET switch) and the output terminal 534 of the second switch 532 (the drain terminal in the case of a MOSFET switch) may be coupled together to form a single stimulation channel output 284.

In at least one embodiment, selection of which of the positive amplitude waveform 308 or the negative amplitude waveform 316 is outputted as the stimulation signal at the stimulation channel output 284 at a given time is made through appropriate timing of the non-zero pulses of the positive pulse signal 342 driving the first driver module 440 and the negative pulse signal 344 driving the second driver module 540. For example, when it is desired that only one of the positive amplitude waveform 308 or the negative amplitude waveform 316 is outputted at the stimulation channel output 284 at a given time, only one of the positive pulse signal 342 and the negative pulse signal 344 is allowed to have a non-zero pulse at any given time.

According to at least one example embodiment, the microcontroller 210 may implement a finite state machine having at least an inter-pulse state, a positive state, and a negative state. Each of the states are exclusive of one another and the microcontroller 210 can only be in one of the states at any given time.

In the inter-pulse state, the microcontroller 210 outputs the second control signals 262a and 262b to have a positive pulse signal 342 having a zero value and a negative pulse signal 344 also having a zero value. It will be appreciated that this corresponds to the portion of pulse signals 342, 344 between non-zero pulses. In this state, both the first switch 432 and the second switch 532 are configured to be in the open position. Accordingly, neither of the positive amplitude waveform 308 and the negative amplitude waveform 316 are output as the stimulation signal at the stimulation channel output 284. The inter-pulse state can also correspond to an idle state of the stimulation unit 110 when a reference value (e.g. 0 V) is outputted as the stimulation signal.

In the positive state, the microcontroller 210 outputs a negative pulse signal 344 having a zero value as part of the second control signal 262b. In this state, the microcontroller 210 is allowed to output a positive pulse signal 342 having a non-zero value as part of the second control signal 262b. In this state, the first switch 432 may be controlled to move to the closed position and the second switch 532 is controlled to move to the open position. Consequently, the positive amplitude waveform 308 is outputted as the stimulation signal at the stimulation channel output 284.

In the negative state, the microcontroller 210 outputs a positive pulse signal 342 having a zero value as part of the second control signal 262a. In this state, the microcontroller 210 is allowed to output a negative pulse signal 344 having a non-zero value as part of the second control signal 262b. In this state, the second switch 532 may be controlled to move to the closed position and the first switch 432 is controlled to move to the open position. Consequently, the negative amplitude waveform 316 is outputted as the stimulation signal at the stimulation channel output 284.

In at least one embodiment, the finite state machine of the microcontroller 210 is composed of only the inter pulse state, the positive pulse state, and the negative pulse state. Limiting the finite state machine to only these three states ensures that at most one of the positive amplitude waveform 308 and the negative amplitude waveform 316 is outputted at the stimulation channel output 284 any given time. This is advantageous, as ensuring that only one of the positive amplitude waveform 308 and the negative amplitude waveform 316 is outputted at the stimulation channel output 284 at any given time guards against device overload (high current through switches 432 and 532 at the same time), which may damage one or more components of the system.

Figure 7B:
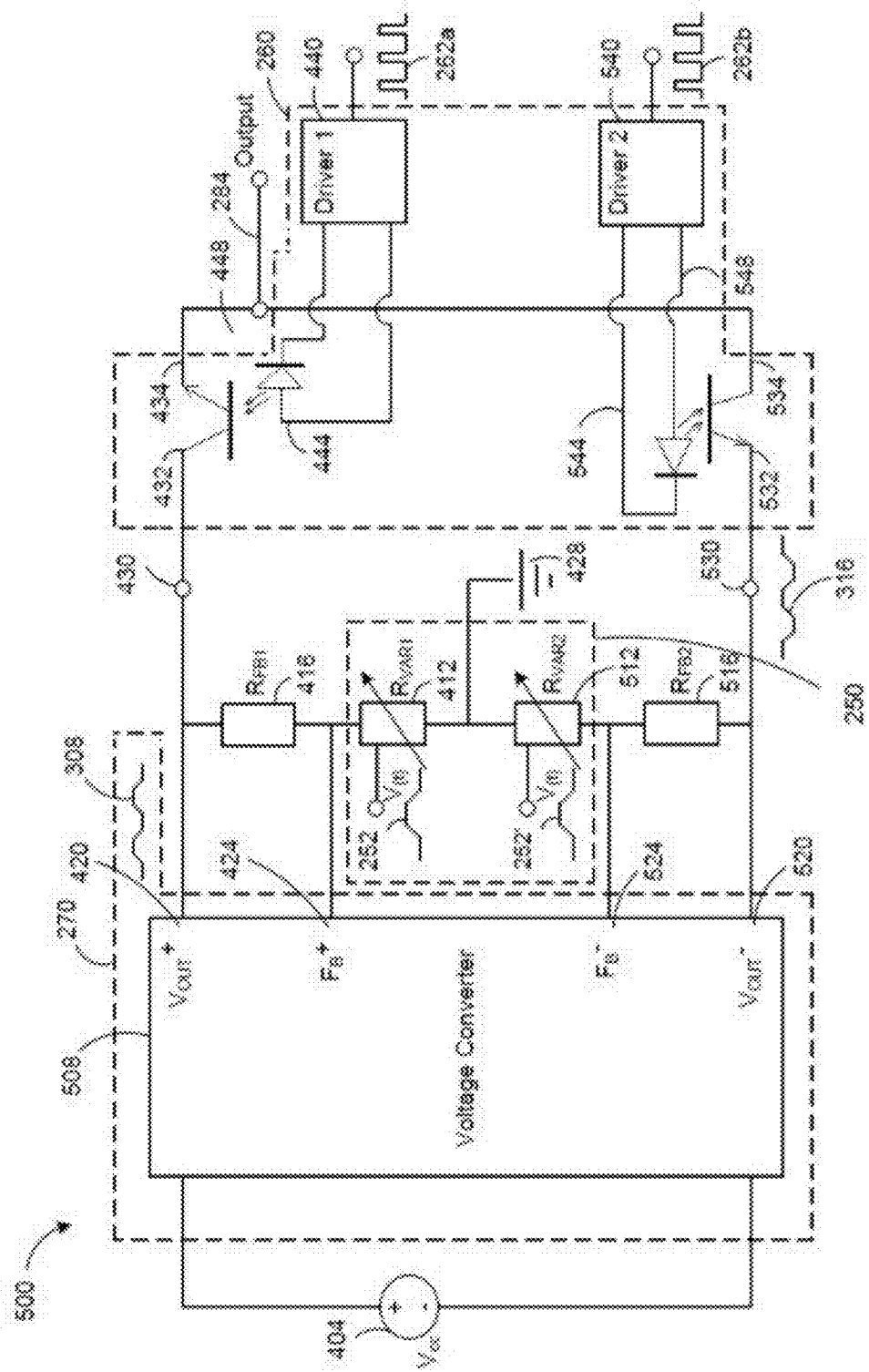
FIG. 7B illustrates a schematic circuit diagram of a sub-module of the electrical stimulation system according to an alternative example embodiment.

Referring now to FIG. 7B, therein illustrated is a circuit diagram of an alternate example embodiment of the signal generation module 500. According to this alternate example embodiment, the first switch 432 is implemented as a first solid-state relay driven by a first optocoupler 460 and the second switch 532 is implemented as a second solid-state relay driven by a second optocoupler 560. Advantageously, use of optocouplers 460, 560 provides faster turn off time while reducing the number of components required.

Figure 8:
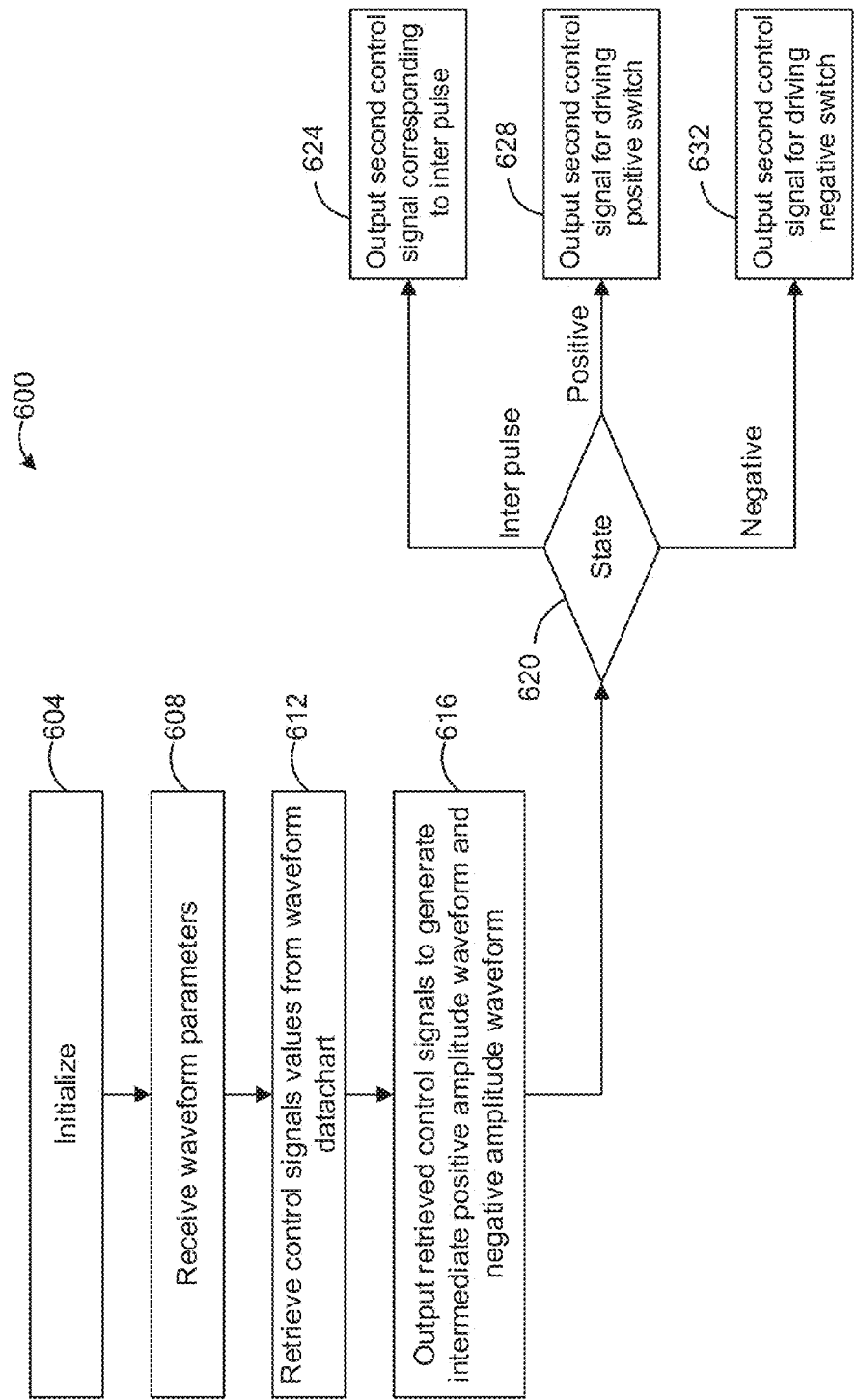
FIG. 8 illustrates a flowchart showing an example embodiment of a method for generating stimulation signals for an FES system.

Referring now to FIG. 8, therein illustrated is a flowchart of an example embodiment of a method 600 for controlling the generation of a stimulation signal for an FES system. For example, the microcontroller 210 of the stimulation unit 110 can be configured to carry out the method 600.

At 604, the microcontroller 210 outputs control signals to initialize the various elements of the signal generation sub-module 240. For example, the microcontroller 210 sends initializing signals to the voltage converter 508 and the potentiometer forming the voltage conversion module. The microcontroller 210 can further send initializing signals to the switch driver module. The initialization signals may be outputted in addition to the first control signal 252 and the second control signal 262.

At 608, the microcontroller 210 receives a currently selected set of stimulation parameters. The set of stimulation parameters may be pre-selected, selected according to trigger signals received at the microcontroller 210 from another unit of the FES system 102, or received in real-time from another unit of the FES system 102. The selection of the set of stimulation parameters may be intermittently updated. For example, the controller unit 130 may send commands and updated data to the stimulation unit 110 to change the current set of stimulation parameters. The current set of stimulation may also be changed by some special situation, such as different terrain or a different mode or operation, for example.

At 612, the microcontroller 210 determines the values of the first control signal 252 and the second control signal 262 according to the characteristics defined in the selected set of stimulation parameters. For example, the values of the first control signal 252 and the second control signal 262 corresponding to the defined stimulation parameters can be retrieved from the stored waveform data chart.

At 616, the first control signal 252 is outputted. The first control signal 252 is received at the voltage conversion module for generating the intermediate positive amplitude waveform 308 and the intermediate negative amplitude waveform 316.

At 620, the current state of the finite state machine of the microcontroller 210 is queried. If the finite state machine of the microcontroller 210 is in the inter pulse state, the method proceeds to 624. If the finite state machine of the microcontroller 210 is in the positive pulse state, the method proceeds to 628. If the finite state machine of the microcontroller 210 is in the negative pulse state, the method proceeds to 632.

At 624, the finite state machine of the microcontroller 210 is in the inter pulse state and the microcontroller 210 outputs the second control signal 262 to have a zero value in the positive pulse signal 342 and a zero value in the negative pulse signal 344.

At 628, the finite state machine of the microcontroller 210 is in the positive pulse state and the microcontroller 210 outputs a positive pulse signal 342 having a non-zero value in the second control signal 262 but is restricted from outputting a negative pulse signal 344 having a zero value at the same time.

At 632, the finite state machine of the microcontroller 210 is in the negative pulse state and the microcontroller 210 outputs a negative pulse signal 344 having a non-zero value in the second control signal 262 but is restricted from outputting a positive pulse signal 342 having a zero value at the same time.

According to various example embodiments, acts 616 to 632 may be repeated to continue outputting first control signals 252 and second control signals 262 to the signal generation submodule 240 while the user 170 is using the FES system. Additionally, the method 600 may periodically return to acts 608 and 612 to receive updated stimulation parameters and further adjust the first control signals 252 and second control signals 262 based on the updated stimulation parameters.

A non-zero positive pulse signal 342 or a non-zero negative pulse signal 344 to output the positive amplitude waveform 308 and the negative amplitude waveform 316 may be subject to transient forces. According to various embodiments, the transient time is selected to be about 50 μs. For example, the transient time can be selected to be between 50 μs and 200 μs.

According to one example embodiment, where the voltage converter module 408 has a similar transient time performance, it is possible to only turn on the voltage converter module 408 to output the positive amplitude waveform 308 when the finite state machine is in the positive pulse state and to only turn on the voltage converter module 408 to output the negative amplitude waveform 316 when the finite state machine is in the negative pulse state. When the finite state machine is in the inter pulse state, the voltage converter module 408 is turned off. Advantageously, turning on the voltage converter module 408 only in the positive pulse state or negative pulse state provides for a saving in power.

According to an alternative embodiment, the opening and closing of the first switch 432 and second switch 532 may be coordinated to reduce the voltage fall time at the stimulation channel output 284. Without modification to reduce fall time, when the first switch 432 is closed to output a positive converted voltage outputted from the first output terminal 420, the voltage at the stimulation channel output 284 will gradually fall back to zero amplitude value. Likewise without modification to reduce fall time, when the switch 532 is closed to output a negative converted voltage outputted from the first output terminal 420, the voltage at the stimulation channel output 284 will gradually fall back to zero amplitude value. The time required to reach zero amplitude value defines the voltage fall time. This time is generally constrained by the characteristics of the components connected to the stimulation channel output 284, such as the switches 432, 532. For example, a typical voltage fall time for a MOSFET switch that is driven by a Dual, high Voltage, Isolated MOSFET Driver is on the order of several milliseconds while a typical fall time for an optocoupler is approximately 100 us or higher (ex: 80 us or higher).

Figure 9:
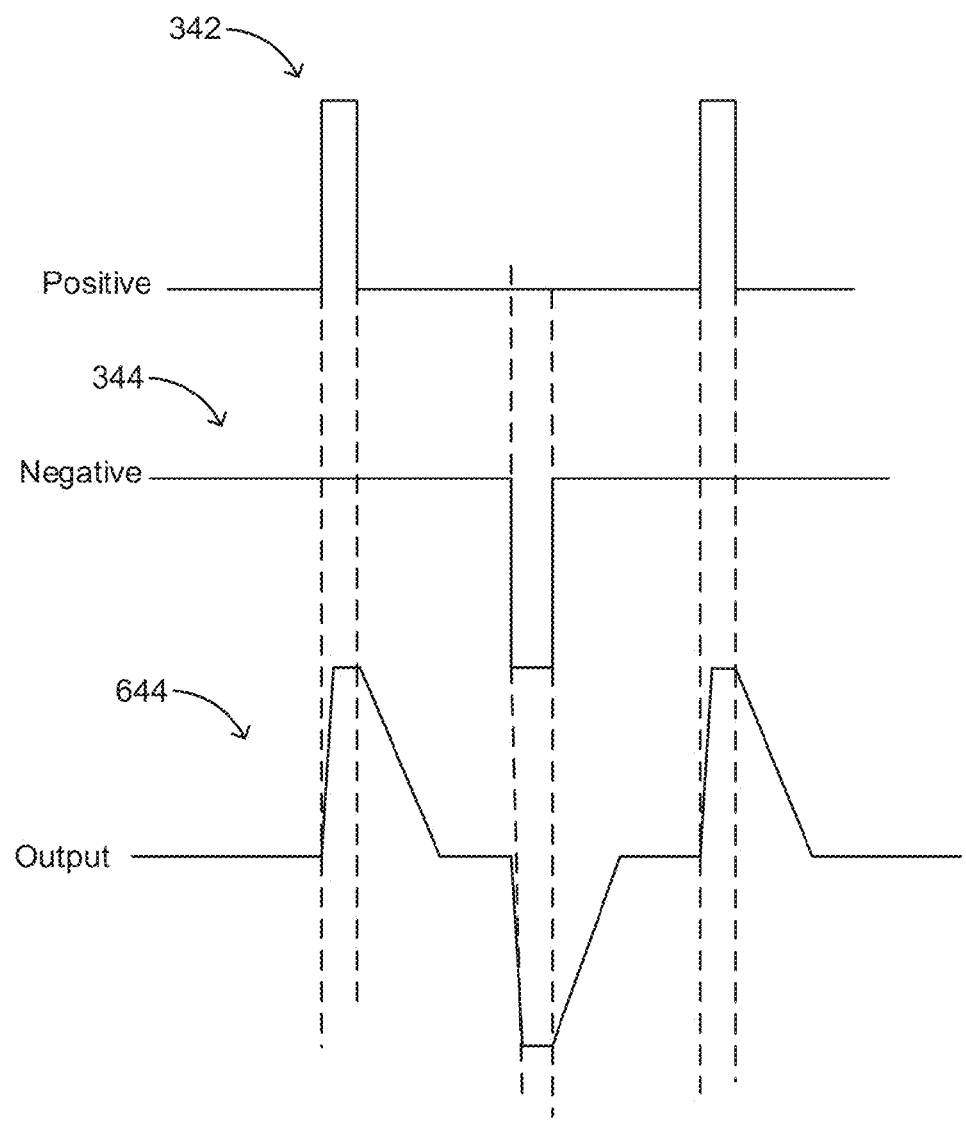
FIG. 9 illustrates an example positive pulse signal waveform, an example negative pulse signal waveform, and an example output waveform.

Referring now to FIG. 9, therein illustrated are an example positive pulse signal waveform 342, an example negative pulse signal waveform 344 corresponding in time, and an example waveform 644 outputted at the stimulation channel output 284 without any modifications to reduce fall time. For illustrative purposes only, the example outputted waveform 644 has an exaggeratedly long fall time following the end of a non-zero pulse.

Figure 10:
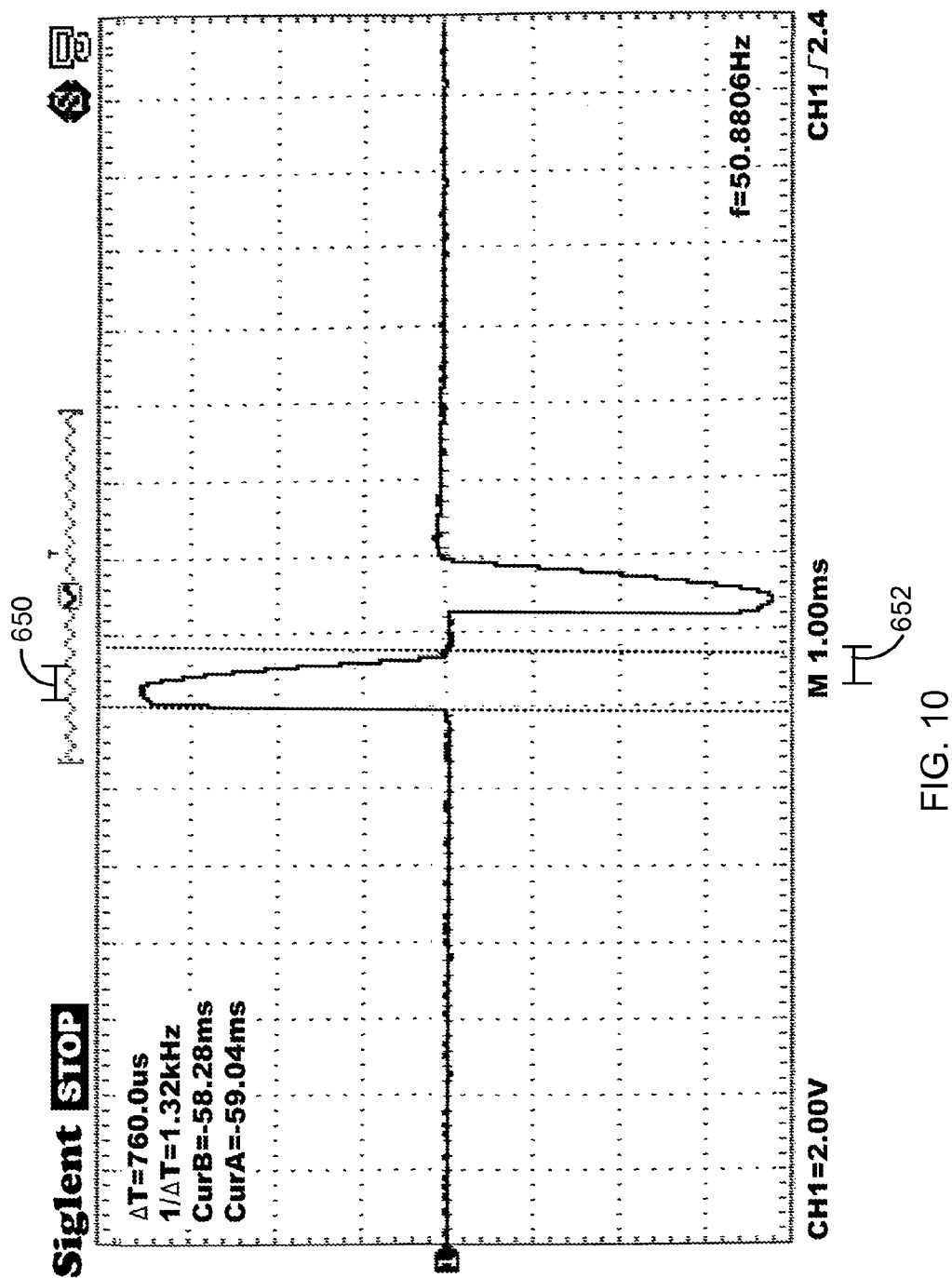
FIG. 10 illustrates an example output plot at the stimulation channel output.

Referring now to FIG. 10, therein illustrated is an example output plot at the stimulation channel output 284 showing the voltage fall times of a representative optocoupler when no modifications have been made to reduce fall time. It will be appreciated that a voltage fall time 650 from a positive outputted signal is on the order of hundreds of microseconds. Similarly, the voltage fall time 652 from a negative outputted signal is also on the order of hundreds of microseconds.

According to various electrical stimulation applications, a shorter rise time and/or fall time may increase precision in the stimulation signal provided to the user 170, which further provides for faster and more accurate response for movement of the user 170. For example, it was observed that a fall time that was less than 50 μs may be beneficial.

According to the teachings herein, to achieve a faster fall time, the first switch 432 may be first controlled to output at the stimulation channel output 284 the positive waveform 308 (i.e. the positive converted voltage of the first output terminal 420) for a duration of a non-zero pulse of the positive pulse signal 342. The second switch 532 may then be controlled to output at the stimulation channel output 284 a negative discharging pulse immediately after the first switch completes outputting the positive waveform 308. That is, the negative discharging pulse is outputted during the voltage fall time of the positive pulse in the outputted positive waveform 308. It was observed that outputting the negative discharging pulse in this fashion shortens the fall time of the positive pulse at the stimulation channel output 284, for example, to a time of less than about 50 μs.

Similarly, the second switch 532 may be controlled to output at the stimulation channel output 284 the negative waveform 316 (i.e. the negative converted voltage of the second output terminal 520) for a duration of the non-zero pulse of the negative pulse signal 344. The first switch 432 may then be controlled to output at the stimulation channel output 284 a positive discharging pulse immediately after the second switch 532 completes outputting the negative waveform 316. That is, the positive discharging pulse may be outputted during the voltage fall time of the negative pulse in the outputted negative waveform 316.

Figure 11:
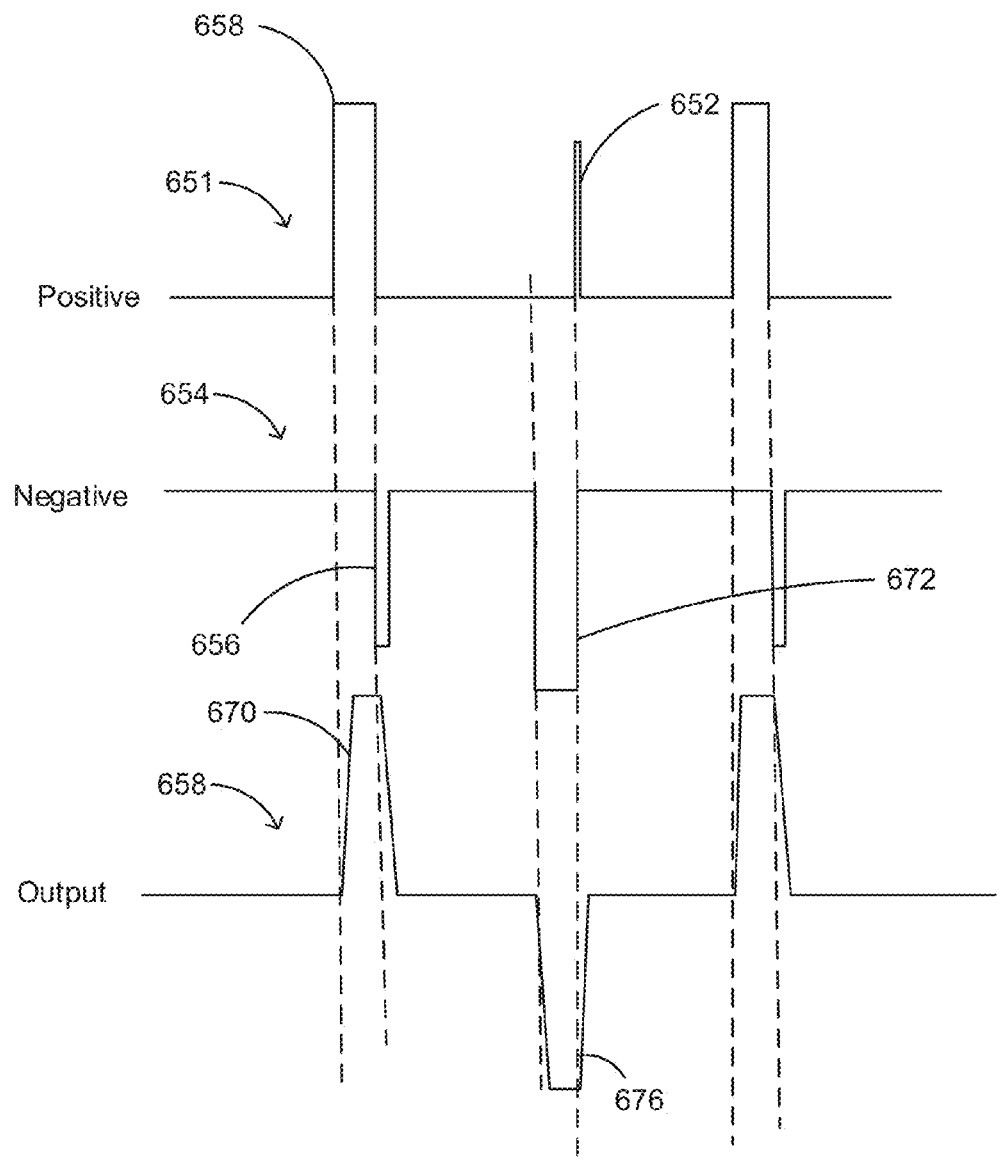
FIG. 11 illustrates an example positive pulse waveform with discharging pulses, an example negative pulse waveform with discharging pulses and an example output waveform.

Referring now to FIG. 11, therein illustrated are an example positive pulse waveform 651 with positive discharging pulses 652, an example negative pulse waveform 654 with discharging pulses 656 corresponding in time, and an example waveform 658 outputted at the stimulation channel output 284. It will be appreciated that the negative pulse waveform 654 includes a first negative discharging pulse 656 that is synchronized in time to start immediately following the end of a first non-zero pulse 658 of the positive pulse waveform 651. The corresponding outputted pulse 670 has a fall time that is substantially shorter than the fall time of an outputted pulse illustrated in FIG. 9.

Similarly, the positive pulse waveform 652 includes a first positive discharging pulse 652 that is synchronized in time to start immediately following the end of a non-zero pulse 672 of the negative pulse waveform 654. The corresponding outputted pulse 676 also has a fall time that is substantially shorter than the fall time of an outputted pulse illustrated in FIG. 9.

Figure 12:
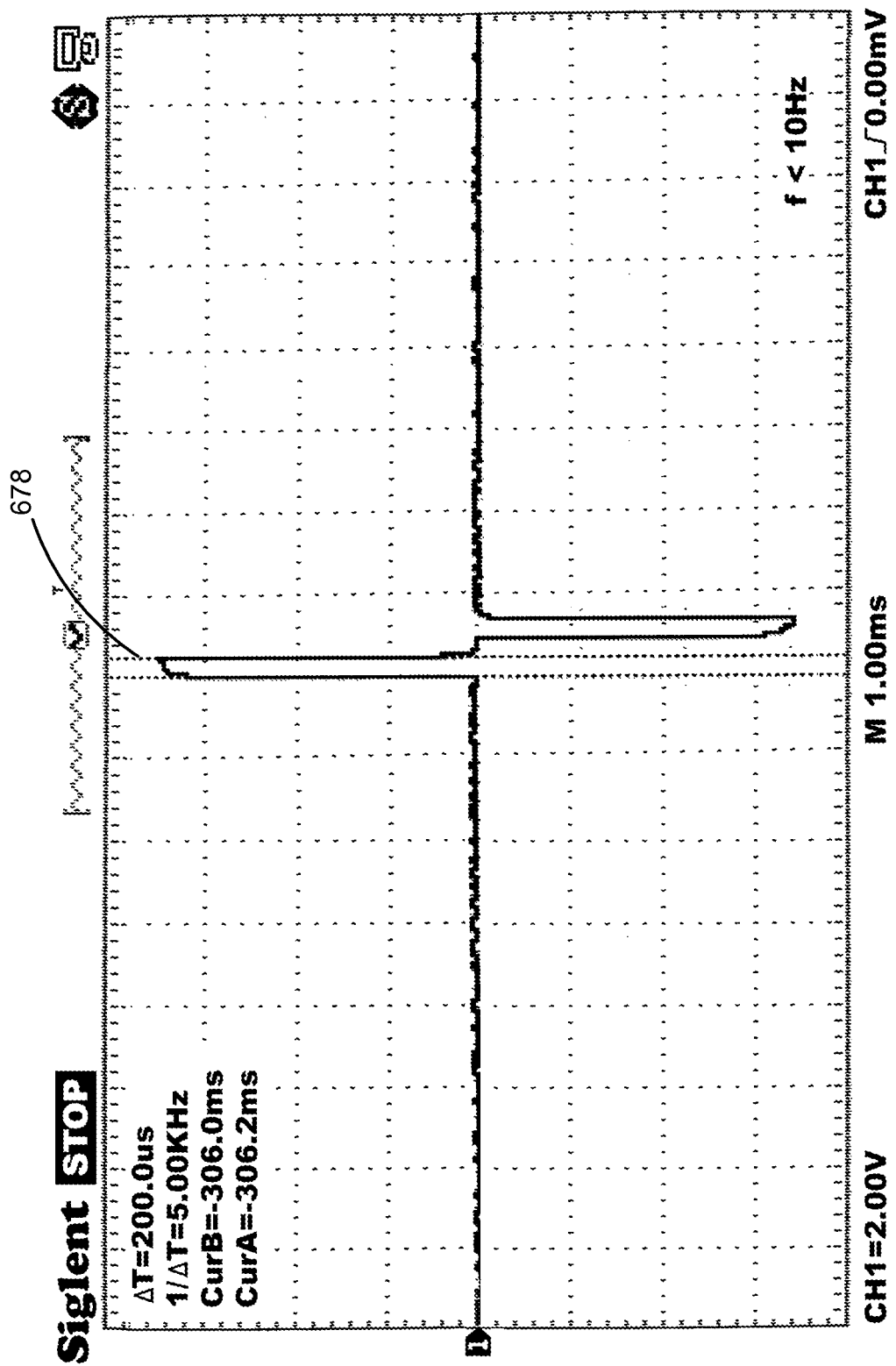
FIG. 12 illustrates an example output plot at the stimulation channel output.

Referring now to FIG. 12, therein illustrated is an example output plot at the stimulation channel output 284 showing the voltage fall times of a representative optocoupler when aided by discharging pulses. It will be appreciated that a voltage fall time 678 is substantially shorter than the voltage fall time 650 illustrated in FIG. 10.

Figure 13:
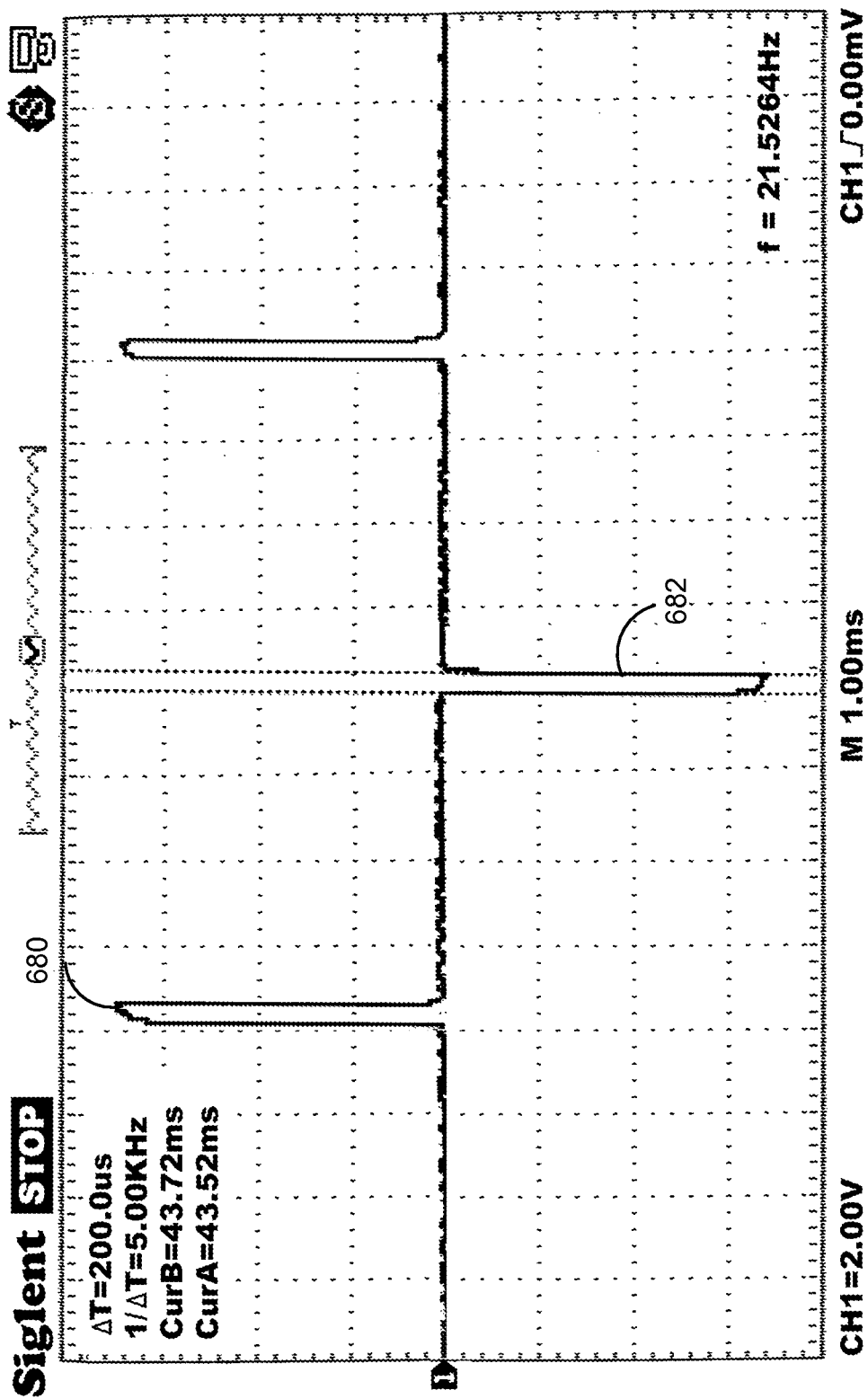
FIG. 13 illustrates another example output plot at the channel output 284.

Referring now to FIG. 13, therein illustrated is an example output plot at the stimulation channel output 284 showing both a positive pulse 680 of the outputted positive waveform 308 and a negative pulse 682 of the outputted negative waveform 316. It will be appreciated that the voltage fall time for both the outputted positive pulse 680 and outputted negative pulse 682 are on the order of tens of microseconds (i.e. less than 50 μs), thereby achieving increased precision. Accordingly, providing a discharging pulse of the opposite sign immediately following the completion of an outputted pulse substantially shortens the voltage fall time of the outputted pulse at the stimulation channel output 284.

According to various example embodiments, the duration, or width, of a negative discharging pulse 656 is substantially shorter than the duration of a corresponding non-zero pulse 658 of the positive pulse waveform 651. The duration of the negative discharging pulse 656 is chosen so as to avoid outputting an undesired negative pulse at the stimulation channel output 284 immediately following the outputting of the positive waveform 308. For example, to avoid outputting the negative pulse, the duration of the negative discharging pulse 656 is chosen to be shorter than a fall time from the positive waveform 308.

Similarly, the duration, or width, of a positive discharging pulse 652 is substantially shorter than the duration of a corresponding non-zero pulse 672 of the negative pulse waveform 654. The duration of the positive discharging pulse 652 is chosen so as to avoid outputting an undesired positive pulse at the stimulation channel output 284 immediately following the outputting of the negative waveform 316. For example, to avoid outputting the positive pulse, the duration of the positive discharging pulse 652 is chosen to be shorter than a fall time from the negative waveform 316.

According to various example embodiments, the duration of a negative discharging pulse 656 may be chosen based on the amplitude of the positive waveform 308 (i.e. the converted voltage outputted from the first output terminal 420) at a corresponding point in time. As described herein above, the positive converted voltage outputted from the first output terminal 420 is a time varying signal that may be defined by a desired amplitude u 322, a rise time tt1 324, a hold time tt2 328, a fall time tt3 332, and an idle time tt4 336. The amplitude of the positive waveform at the moment of a given non-zero pulse 658 of the positive pulse waveform 651 may be different depending on whether that non-zero pulse 658 occurs during the rise time tt1 324, a hold time tt2 328, a fall time tt3 332, or an idle time tt4 336. Accordingly, the duration of the negative discharging pulse 656 corresponding in time to that non-zero positive pulse 658 (i.e. immediately following that non-zero positive pulse 658) is chosen based on the amplitude value of the positive waveform 308 outputted at the time. That is, the duration of the negative discharging pulse 656 may be chosen based on the amplitude of the stimulation signal at a corresponding point in time. The duration of a positive discharging pulse 652 may be chosen in a similar manner based on the amplitude of the negative waveform 316 at a corresponding point in time.

According to one example embodiment, it was observed that the duration of a given negative discharge pulse 656 (or positive discharge pulse 652) increased quadratically with an increase in the amplitude value of the positive waveform 308 (or negative waveform 316). For example, it may be possible to calculate a suitable duration of a negative discharge pulse 656 (or positive discharge pulse 652) based on a given amplitude value of the positive waveform 308 (or negative waveform 316) at a corresponding point in time. An example of such a relation is shown in equation 4 and calculated and actual values are shown in Table 2.

$$\text{Duration (μs)} = 3 + \text{Intensity}^2/4 \qquad (4)$$

TABLE 2

Discharge Pulse Duration Based on Pulse Intensity

| Intensity | Calculated Value (μs) | Actual Value (μs) |
|---|---|---|
| 1 | 3.25 | 3 |
| 2 | 4 | 4 |
| 3 | 5.25 | 5 |
| 4 | 7 | 7 |
| 5 | 9.25 | 9 |
| 6 | 12 | 11 |
| 7 | 15.25 | 15 |

TABLE 2-continued

Discharge Pulse Duration Based on Pulse Intensity

| Intensity | Calculated Value (μs) | Actual Value (μs) |
|---|---|---|
| 8 | 19 | 19 |
| 9 | 23.25 | 23 |

According to one example embodiment where the stimulation parameters define characteristics of a cycle of the stimulation signal, the stimulation parameters may further define the durations of the negative discharging pulses 656 (or positive discharging pulses 652) across the cycle of the stimulation signal. Given the amplitude values of the stimulation signal over the cycle, each negative discharging pulse 656 (or positive discharging pulse 652) may have a duration that is defined based on an amplitude of the stimulation signal at a corresponding point in time within the cycle of the stimulation signal. For example, the durations of one or more negative discharging pulses 656 may be defined based on the second control signal 262 outputted from the microcontroller 210.

For example, the second control signal 262 may have a first switch control signal component for controlling the first switch 432. The first switch control signal component may define a duration of the interval between the start of two adjacent non-zero positive pulses (i.e. desired period), the duration of a non-zero positive pulse (i.e. desired pulse width) and a plurality of discharging pulse widths of the positive discharging pulses over the cycle of the stimulation signal. The second control signal 262 may further have a second switch control signal component for controlling the second switch 532. The second switch control signal component may define a duration of the interval between the start of two adjacent non-zero negative pulses, the duration of a non-zero negative pulse and a plurality of discharging pulse widths of the negative discharging pulses over the cycle of the stimulation signal. The second control signal 262 may further define (e.g. as part of the first switch control signal or the second switch control signal) a duration of time between a non-zero positive pulse and a non-zero negative pulse (i.e. a phase offset).

According to one example embodiment, the microcontroller 210 may implement a finite state machine having at least a positive state, an inter-pulse positive state, a negative state and an inter-pulse negative state. Each of the states are exclusive of one another and the microcontroller 210 can only be in one of the states at any given time.

In the positive state, the microcontroller 210 outputs a positive pulse signal 344 having a zero value as part of the second control signal 262a which results in the output of the positive pulse signal 342. In this state, the first switch 432 may be controlled to move to the closed position (e.g. the switch 432 is on) and the second switch 532 is controlled to move to the open position (e.g. the switch 532 is off). Consequently, the positive amplitude waveform 308 is outputted as the stimulation signal at the stimulation channel output 284.

In the inter-pulse positive state, the microcontroller 210 flows through several sub-states. In the first sub-state, the microcontroller 210 outputs the second control signals 262a and 262b to have a positive pulse signal 342 having a zero value and a negative pulse signal 344 also having a zero value. In this first sub-state, both the first switch 432 and the second switch 532 are configured to be in the open position (e.g. the switches 432 and 532 are off). Immediately after entering the first-sub-state, the microcontroller 210 enters a second sub-state to output a second control signal to have a negative pulse signal 344 having a non-zero value, thereby outputting a negative discharging pulse. The duration of the second sub-state corresponds to a duration of the negative discharging pulse. The microcontroller 210 then leaves the second sub-state and enters a third sub-state to output the second control signals 262a and 262b to have a positive pulse signal 342 having a zero value and a negative pulse signal 344 also having a zero value.

In the negative state, the microcontroller 210 outputs a positive pulse signal 342 having a zero value and the second control signal 262b to output a negative pulse signal 344 having a non-zero value. In this state, the first switch 532 may be controlled to move to the closed position (e.g. the switch 532 is on) and the first switch 432 is controlled to move to the open position (e.g. the switch 432 is off). Consequently, the negative amplitude waveform 316 is outputted as the stimulation signal at the stimulation channel output 284.

In the inter-pulse negative state, the microcontroller 210 flows through several sub-states. In the first sub-state, the microcontroller 210 outputs the second control signals 262a and 262b to have a positive pulse signal 342 having a zero value and a negative pulse signal 344 also having a zero value. In this first sub-state, both the first switch 432 and the second switch 532 are configured to be in the open position (e.g. the switches 432 and 532 are off). Immediately after entering the first-sub-state, the microcontroller 210 enters a second sub-state to output a second control signal to have a positive pulse signal 342 having a non-zero value, thereby outputting a positive discharging pulse. The duration of the second sub-state corresponds to a duration of the positive discharging pulse. The microcontroller 210 then leaves the second sub-state and enters a third sub-state to output the second control signals 262a and 262b to have a positive pulse signal 342 having a zero value and a negative pulse signal 344 also having a zero value.

Figure 14:
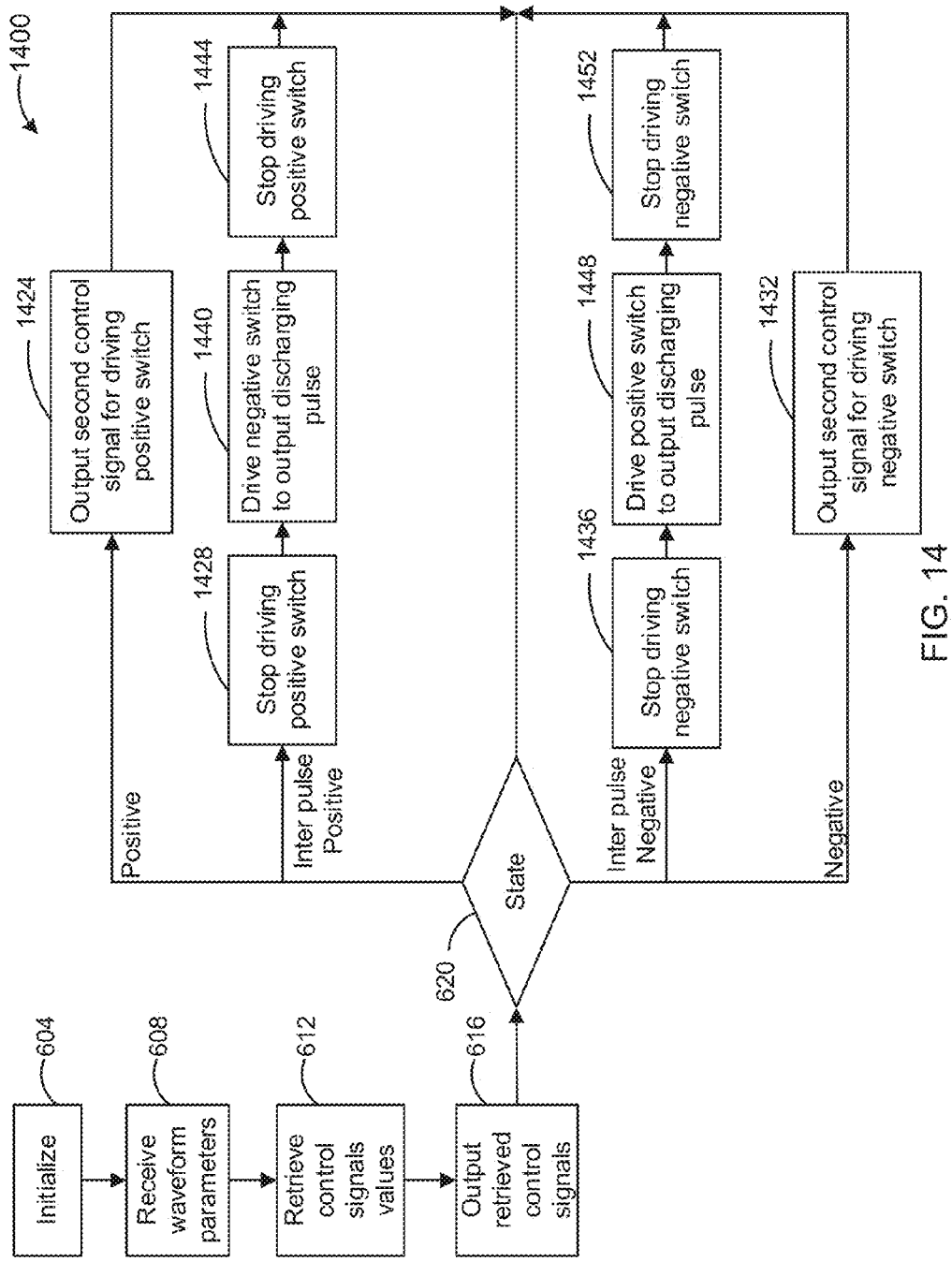
FIG. 14 illustrates a flow chart of an example embodiment of a method for generating stimulation signals for an FES system.

Referring now to FIG. 14 therein illustrated is a flow chart of an example embodiment of a method 1400 for controlling the generation of a stimulation signal for an FES system. For example, the microcontroller 210 of the stimulation unit 110 can be configured to carry out the method 1400. Acts 604 to 616 correspond substantially to acts 604 to 616 as described herein with reference to method 600.

At 620, the current state of the finite state machine of the microcontroller 210 is queried. If the finite state machine of the microcontroller 210 is in the positive state, the method proceeds to 1424. If the finite state machine of the microcontroller 210 is in the inter pulse positive state, the method proceeds to 1428. If the finite state machine of the microcontroller 210 is in the negative state, the method proceeds to 1432. If the finite state machine of the microcontroller 210 is in the inter pulse negative state, the method proceeds to 1436.

At 1424, the finite state machine of the microcontroller 210 is in the positive state and the microcontroller 210 outputs the second control signal 262 to have a non-zero value in the positive pulse signal 342 and a zero value in the negative pulse signal 344.

At 1428, the finite state machine of the microcontroller 210 is in the first sub-state of the inter pulse positive state, and the microcontroller 210 outputs the second control signal 262 to have a zero value in the positive pulse signal 342 and a zero value in the negative pulse signal 344. The microcontroller 210 then enters the second sub-state 1440 to output a negative pulse signal 344 having a non-zero value in the second control signal 262 to output the negative discharging pulse 656 but is restricted from outputting a positive pulse signal 342 having a non-zero value at the same time. The microcontroller 210 then enters the third sub-state 1444 to output the second control signal 262 to have a zero value in the positive pulse signal 342 and a zero value in the negative pulse signal 344.

At 1434, the finite state machine of the microcontroller 210 is in the negative state and the microcontroller 210 outputs the second control signal 262 to have a non-zero value in the negative pulse signal 344 and a zero value in the positive pulse signal 342.

At 1436, the finite state machine of the microcontroller 210 is in the first sub-state of the inter pulse negative state, and the microcontroller 210 outputs the second control signal 262 to have a zero value in the positive pulse signal 342 and a zero value in the negative pulse signal 344. The microcontroller 210 then enters the second sub-state 1448 to output a positive pulse signal 342 having a non-zero value in the second control signal 262 to output the positive discharging pulse 652 but is restricted from outputting a negative pulse signal 344 having a non-zero value at the same time. The microcontroller 210 then enters the third sub-state 1452 to output the second control signal 262 to have a zero value in the positive pulse signal 342 and a zero value in the negative pulse signal 344.

EXAMPLE 1

Figures 1, 15:
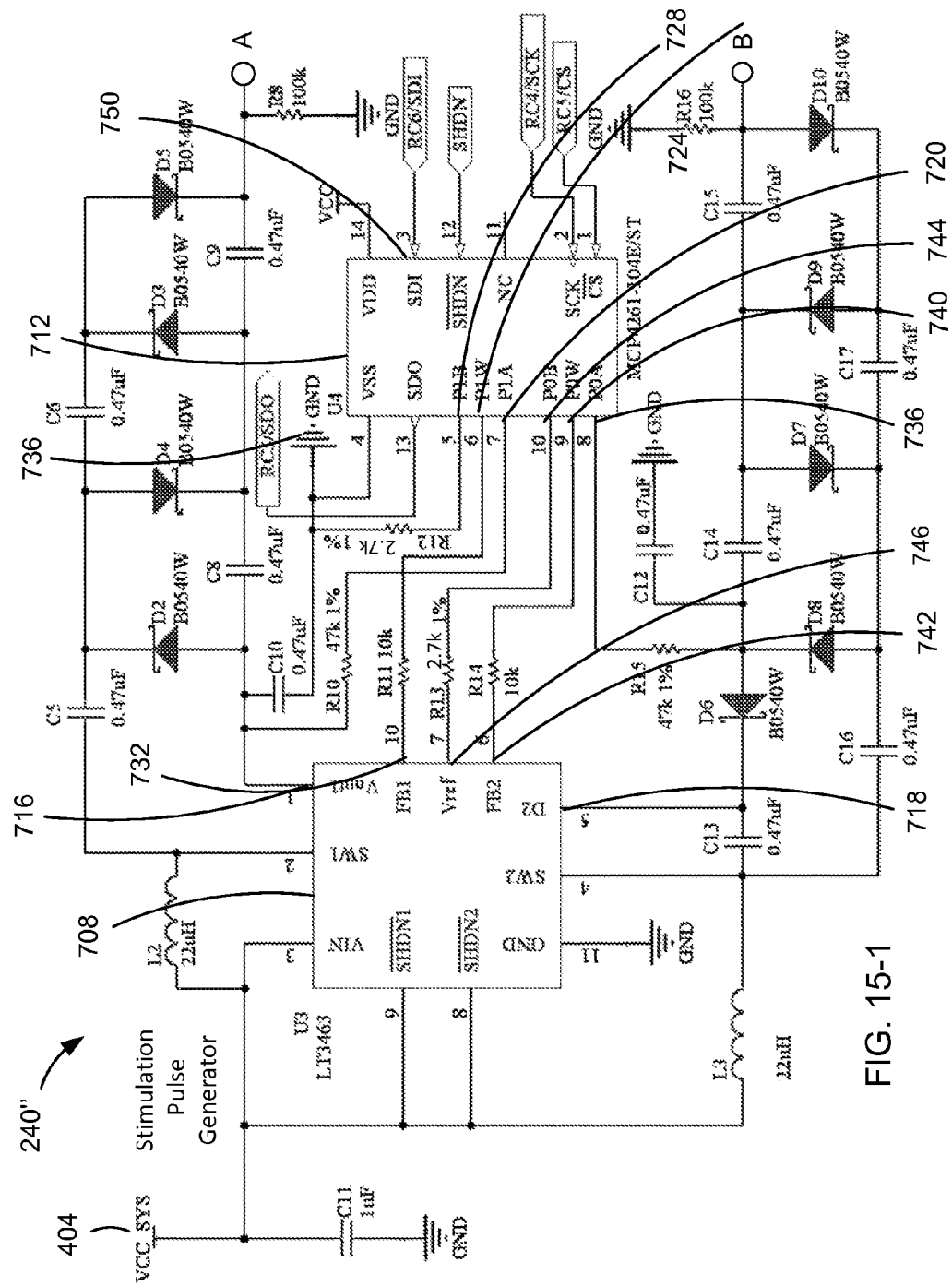
Figures 2, 15:
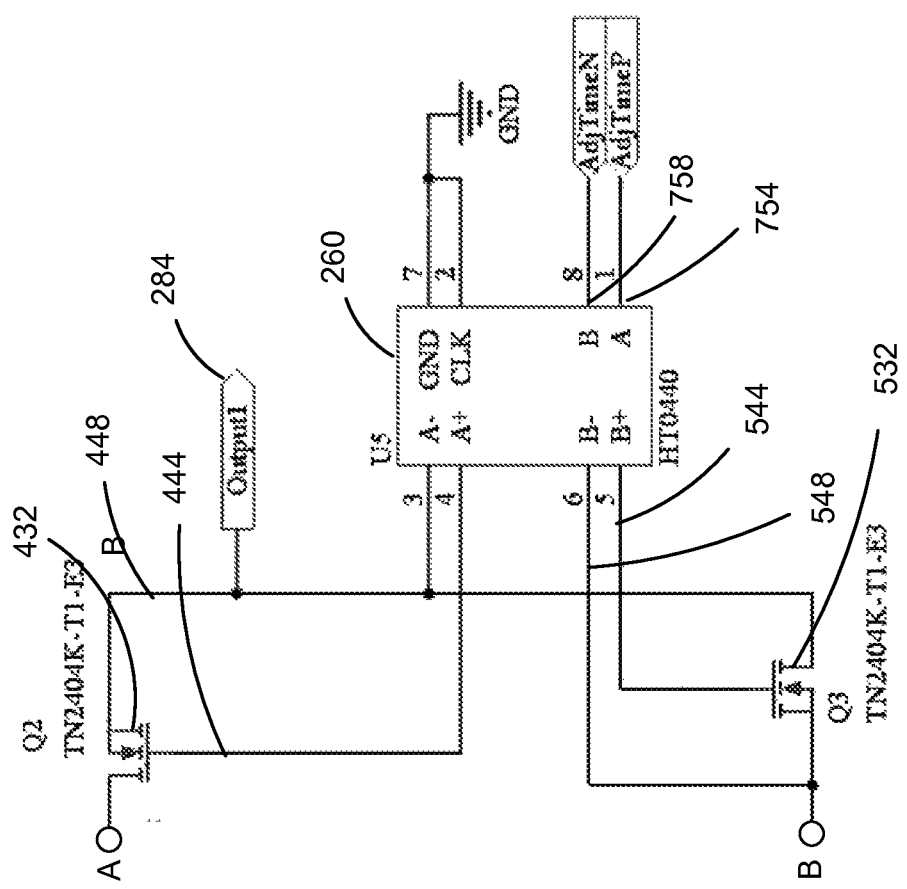

Referring now to FIGS. 15-1 and 15-2, therein illustrated is a circuit diagram of an example implementation of the signal generation submodule 240″. According to the example implementation, the voltage converter is implemented using a dual DC/DC convertor 708 such as a Linear Technology LT3463 Dual Micropower DC/DC Convertor having Schottky Diodes. The dual DC/DC convertor 708 receives voltage from a voltage supply 404 and outputs a positive converted voltage, which may represent the positive amplitude waveform 308 at positive voltage output 716. The dual DC/DC convertor 708 also outputs a negative converted voltage, which may represent the negative amplitude waveform 316 at the negative voltage output 718.

The first and second variable resistors 412, 512 are implemented using a dual potentiometer 712 such as Microchip MCP426X Dual SPI Digital Potentiometer with Non-Volatile Memory. A positive converted voltage output 716 of the dual DC/DC convertor 708 is coupled to a first terminal 720 (P1A) of the first internal potentiometer. A wiper terminal 724 (P1W) of the first internal potentiometer is coupled to a first feedback terminal 732 of the dual DC/DC convertor 708. A second terminal 728 (P1B) of the first internal potentiometer is coupled to ground 736. The internal resistance of the first internal potentiometer of the dual potentiometer 712 can be controlled to achieve a desired ratio of resistances. According to the selection of resistance values of intermediate resistors, the value of the converted voltage outputted at voltage output 716 can be calculated according to equation 5.

$$Vout = 1.25 * \left(1 + \frac{147 - R}{2.7 + R}\right) \tag{5}$$

Equation 5 may be derived from equation 6:

$$V_{out} = V_{in}\left(1 + \frac{R_{FB}}{R_{Var}}\right) \tag{6}$$

wherein $V_{in}$ is equal to 1.25 V. $R_{FB}$ is equal to the resistance between the positive voltage output 716 and the wiper terminal 724. The parameter $R_{Var}$ is equal to the resistance between the wiper terminal 724 and ground (GND). For this example embodiment, given that the resistance between the first terminal 720 and the second terminal 728 is 100 kΩ and that the resistor between the wiper terminal 724 and the second terminal 728 is equal to R (an internal variable resistance of the Potentiometer), the resistor $R_{FB}$ in this case is equal to 100 kΩ−R+47 kΩ (the value of the resistor R10 between the positive voltage output 716 and the first terminal 716). The parameter $R_{Var}$ is equal to R+2.7 kΩ (the value of the resistor R12 connecting the second terminal 728 and GND).

Referring now to Table 3, therein illustrated is an example waveform data chart showing resistance values R for different desired voltage amplitude values. The variable resistor within the MCP426X Dual SPI Digital Potentiometer is configured using a resistor network having a resistor ladder formed of a series of equal value resistors. A desired resistance value R of the potentiometer can be achieved by selecting an appropriate number of the equal value resistors. For an 8-bit device, the resolution of the equal value resistors may be 3900. The Mcp4261-calculated values in Table 3 represent a desired number of the equal value resistors to achieve the desired value R. The Mcp4261_Real_value represents an actual selected number of equal value resistors to achieve the desired value R given the resolution of the device.

A negative converted voltage output 718 of the dual DC/DC convertor 708 is coupled to a first terminal 736 (P0A) of the second internal potentiometer. A wiper terminal 740 (P0W) of the second internal potentiometer is coupled to a second feedback terminal 742 of the dual DC/DC convertor 708. A second terminal 744 (P0B) of the first internal potentiometer is coupled to a reference terminal 746 of the dual potentiometer 708. The internal resistance of the second internal potentiometer of the dual potentiometer 712 can be controlled to achieve a desired ratio of resistances. The value of the negative converted voltage outputted at the negative voltage output 718 can be determined in a similar manner as determining the value of the positive converted voltage.

The required resistance values for controlling the dual potentiometer 712 are included in the first control signal 252, which is received as a serial data input at an SPI port 750 of the dual potentiometer 712. Accordingly, the microcontroller 210 can be configured to appropriately format the data in the first control signal 252 in order to be readable by the dual potentiometer 712. The first control signal received at the SPI port 750 may include both the resistance values of the first internal potentiometer for converting the supply voltage to the positive converted voltage and the resistance value of the second internal potentiometer for converting the supply voltage to the second converted voltage.

TABLE 3

Waveform Data Chart for an example MCP426X Potentiometer

| Voltage (V) | R (kΩ) | Mcp4261-calculated | Mcp4261_Real_value (ladder step) |
|---|---|---|---|
| 2 | 90.8625 | 232.9807692 | 235 |
| 3 | 59.675 | 153.0128205 | 156 |
| 4 | 44.08125 | 113.0288462 | 115 |
| 5 | 34.725 | 89.03846154 | 88 |
| 6 | 28.4875 | 73.04487179 | 74 |
| 7 | 24.03214 | 61.62087912 | 62 |
| 8 | 20.69063 | 53.05288462 | 52 |
| 9 | 18.09167 | 46.38888889 | 45 |
| 10 | 16.0125 | 41.05769231 | 42 |
| 11 | 14.31136 | 36.6958042 | 36 |
| 12 | 12.89375 | 33.06089744 | 31 |
| 13 | 11.69423 | 29.9852071 | 28 |
| 14 | 10.66607 | 27.3489011 | 27 |
| 15 | 9.775 | 25.06410256 | 25 |
| 16 | 8.995313 | 23.06490385 | 23 |
| 17 | 8.307353 | 21.30090498 | 21 |
| 18 | 7.695833 | 19.73290598 | 19 |
| 19 | 7.148684 | 18.32995951 | 18 |
| 20 | 6.65625 | 17.06730769 | 17 |
| 21 | 6.210714 | 15.92490842 | 15 |

Continuing with FIGS. 15-1 and 15-2, the positive output terminal 716 is coupled to a terminal of the first switch 432 and the negative output terminal 718 is coupled to a terminal of the second switch 532. The first switch 432 and the second switch 532 are both MOSFET switches. The period controller 260 may be implemented using a Supertex HT0440 Dual, High Voltage, Isolated MOSFET Driver, for example. The MOSFET driver receives a control signal containing information for driving the first switch 432 at a first input terminal 758. The control signal received at the first input terminal 754 may be the first component 262a of the second control signal 262 that is outputted by the microcontroller 210 and that includes the positive pulse signal 342. The MOSFET driver receives a control signal containing information for driving the second switch 532 at a second input terminal 758. The control signal received at the second input terminal 758 may be the second component 262b of the second control signal 262 that is outputted by the microcontroller 210 and that includes the negative pulse signal 344. A first positive voltage output (A+) is coupled to a gate terminal of the MOSFET switch 432 and sends the first intermediate control signal 444 thereto. A first negative voltage output (A−) is coupled to a source terminal of the MOSFET switch 432 and sends the second intermediate control signal 448 thereto. A second positive voltage output (B+) is coupled to a gate terminal of the MOSFET switch 432 and sends the first intermediate control signal 548 thereto. A second negative voltage output (B−) is coupled to a second source terminal of the MOSFET switch 532 and sends the second intermediate control signal 544 thereto.

The source terminal of the first switch 432 and the drain terminal of the second switch 532 are coupled together and form the stimulation channel output 284.

Figures 1, 16:
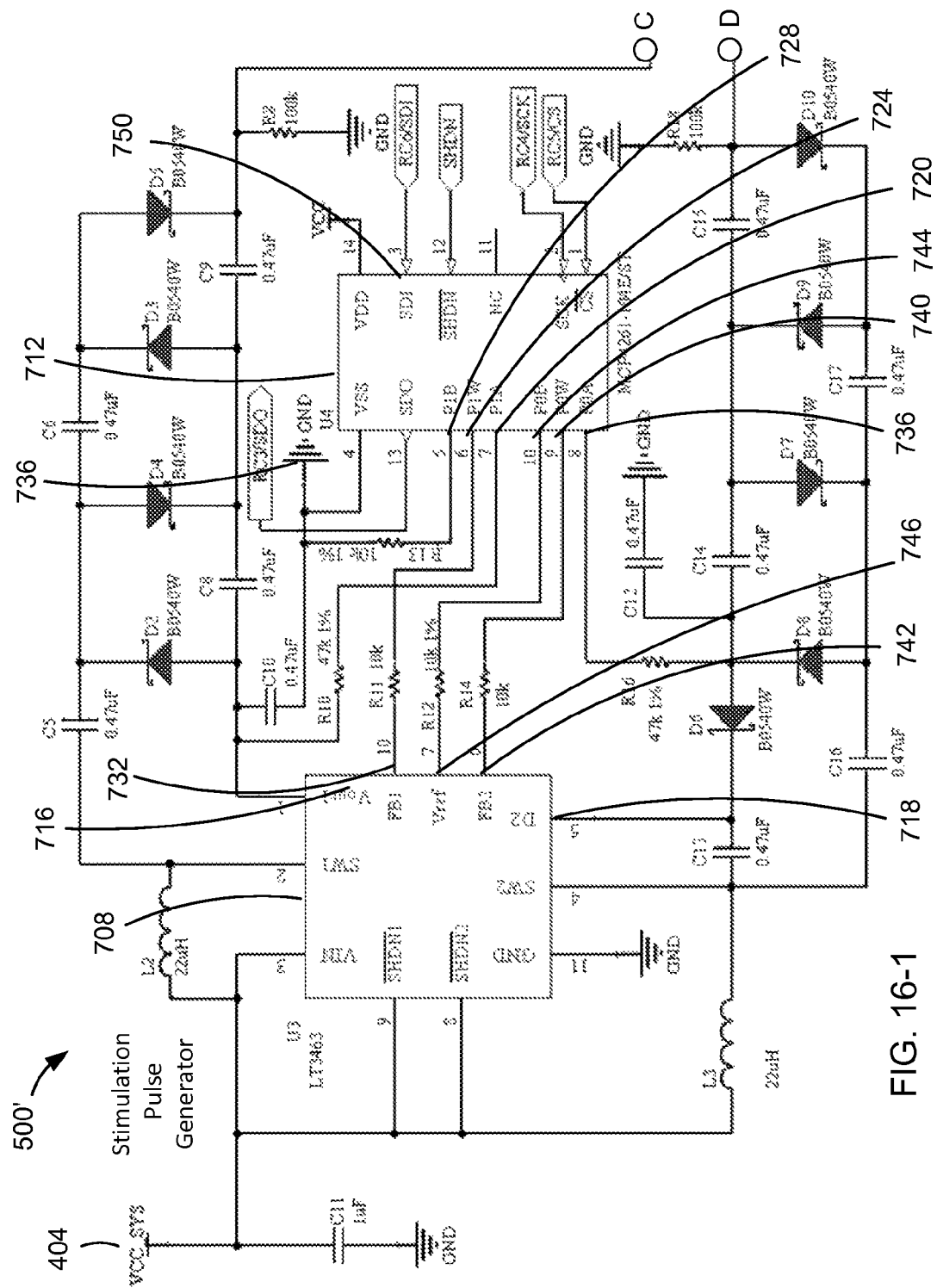
Figures 2, 16:
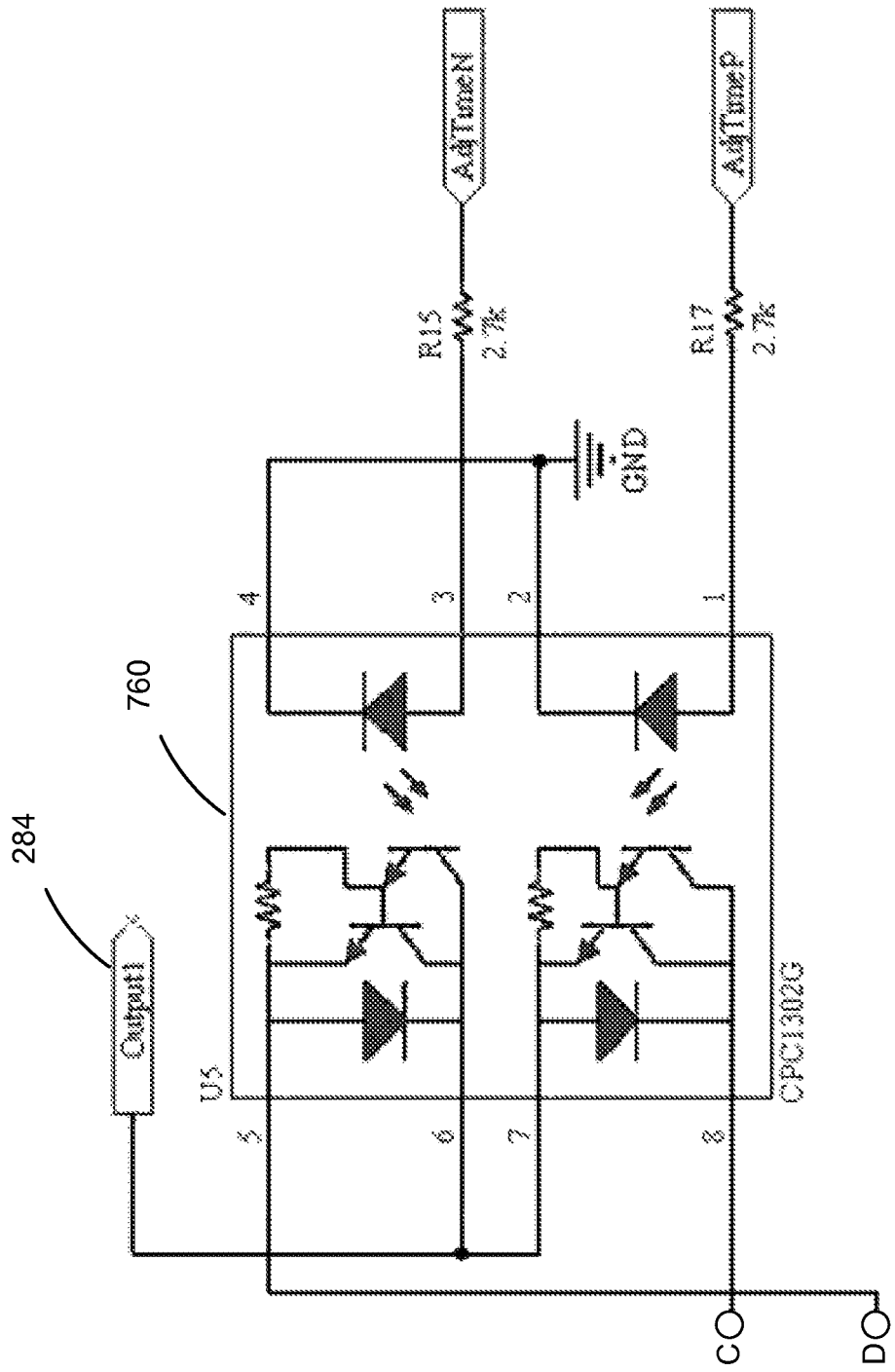

Referring now to FIGS. 16-1 and 16-2, therein illustrated is a circuit diagram of an alternate example embodiment of a signal generation module 500'. According to this alternate example embodiment, the first switch 432, second switch 532 and the period controller 260 is implemented as a unitary dual optocoupler 760 having a high-voltage Darlington output stage. For example, the dual optocoupler 760 may be implemented by a CPC1302 optocoupler from IXYS instead of using the HT0440 The CPC1302 is much faster than the HT0440 and therefore the CPC1302 will allow for a faster turn off time as well as a reduction in components (note that the transistors Q2 and Q3 shown in FIGS. 15-1 and 15-2 do not need to be used in the design shown in FIGS. 16-1 and 16-2).

Further information on the functions performed by the stimulation unit 110 includes the following.

1. Initialize Communication with sensor unit 120 and the control unit 130

The stimulation unit 110 initializes the communication channels for the sensor unit 120 and the control unit 130.

The stimulation unit 110 may also display an error message if any error is detected during communication. For example, the error information may be: "sensor unit 120 xxxxxx is not ready" or "control unit 130 xxxxxx is not ready". Here "xxxxxx" is the id of sensor unit 120 or control unit 130.

2. Communication for stimulation parameters

The Date/Time setting dialog interface is displayed if there is no date/time data (for example the battery is charged after it run out). The stimulation unit 110 then tries to connect to the control unit 130 to download the stimulation parameters if there are no available stimulation parameters. The stimulation unit stops trying to communicate with the control unit 130 if the control unit 130 is not available and then displays: "Please contact your doctor to get the waveform parameters".

3. Orthotic application history record (logging)

The stimulation unit 110 is configured to record the parameters and date/time when the stimulation parameters are changed or adjusted. The stimulation unit 110 then records the time when it starts and stops generating the stimulation signal (except for self-tests). The stimulation unit 110 may also be configured to transfer the records to the control unit 130 before the storage space on the stimulation unit 110 is used up.

4. Output the pulses to Electrodes

The stimulation unit 110 can output the stimulation signal to the electrodes and receive the trigger signals from sensor unit 120. The period T may be decided by trigger signals and the amplitude u may be decided by the current amplitude setting in the stimulation unit 110.

5. Self-Test

There can be various tests that are done such as, but not limited to, a) a Battery Status check; b) a Bluetooth communication channels check; c) a check for electrodes contacted situation by measuring the voltage at a test resistor when a 30 V signal is applied to the electrodes of the stimulation unit 110; and d) Display error messages on the LCD screen and sound an audible alarm if a critical error is detected and possibly flashing the LEDs to indicate the error code.

6. Execute the commands from control unit 130

There are various commands that may be sent to the stimulation unit from the control unit 130 including: a) Mode Change Command to change operation to a particular mode (there may be four modes: Sleep, Training, Walking, and Test); b) Stimulation Control Command to control stimulation including various commands such as, but not limited to, stopping an output stimulation signal, starting to provide an output stimulation signal depending on the operation mode, increasing the amplitude of the stimulation signals and decreasing the amplitude of the stimulation signals pulses, for example; c) Waveform parameter setting commands that can be used to set values for various parameters such as, but not limited to, T, tt1, tt2, tt3, u, tt, t1, and t2; and d) The Date/Time setting Command to set at least one of year, month, day, hour, minute, and second.

7. Display Error Messages

The stimulation unit 110 may display several error messages including error messages for the sensor unit 120. Examples of the error messages include, but are not limited to: a) a battery error message such as "stimulation system 110 Battery is low" in which case the stimulation unit 110 can produce the audible alarm slowly, and "sensor unit 120 Battery is low" in which case the stimulation unit 110 can produce the audible alarm slowly; b) Bluetooth connection error messages such as "sensor unit 120 is not ready" in which case the stimulation unit 110 can produce the Audible alarm quickly, and "control unit 130 is not ready" in which case the stimulation unit 110 can produce the Audible alarm slowly; and c) electrodes are not placed properly error messages such as "Electrodes are not placed properly" in which the stimulation unit 110 can produce the audible alarm quickly.

8. The data format for communication between the sensor unit 120 to/from the stimulation unit 110 and the control unit 130:

target address, source address, "FS", Ax, Ay, Az, F where "FS" means Foot Status;

target address, source address, "BL" where "BL"-means battery low; and target address, source address, "SL" where "SL"-means sleep, force sensor unit 120 into sleep mode.

9. The data format for the stimulation unit 110 to upload the orthotic history records to the control unit 130:

target address, source address, year, month, day, hour, minutes, seconds, T, tt1, tt2, tt3, u, tt, t1, and t2.

Various embodiments of systems, device and methods that can be used to generate a stimulation signal for an FES system have been described here by way of example only. Various modifications and variations may be made to these example embodiments without departing from the spirit and scope of the embodiments, which is limited only by the appended claims. Also, in the various user interfaces illustrated in the figures, it will be understood that the illustrated user interface text and controls are provided as examples only and are not meant to be limiting. Other suitable user interface elements may be possible.

The invention claimed is:

1. An electrical stimulation system for generating a stimulation signal for at least two electrodes for stimulating a body part in a functional electrical stimulation system, the electrical stimulation system comprising:

a controller unit operable for receiving at least one set of stimulation parameters, receiving a trigger signal; and in response to receiving the trigger signal, outputting at least a first control signal and a second control signal based on the at least one set of stimulation parameters;

a voltage conversion module coupled to the controller unit, the voltage conversion module for receiving at least the first control signal and converting a supply voltage based on the received first control signal; and at least one switch receiving the converted supply voltage at a first terminal and selectively outputting based on the second control signal a stimulation signal at a stimulation output terminal.

2. The electrical stimulation system of claim 1, further comprising a driver module controlling the at least one switch based on at least the second control signal, wherein the at least one switch is configured to output the converted voltage as the stimulation signal at the output terminal when the driver module configures the at least one switch to a closed position.

3. The system of claim 1, wherein the at least one set of stimulation parameters comprise a desired amplitude of the stimulation signal and wherein the first control signal is adjusted based on the desired amplitude to correspondingly control certain parameters of the voltage conversion module.

4. The system of claim 3, wherein the at least one set of stimulation parameters further comprise a desired rise time, a desired hold time, a desired drop time, and a desired idle time of a cycle of the stimulation signal and wherein the first control signal is adjusted based on the desired rise time, desired hold time, desired drop time and desired idle time.

5. The system of claim 1, wherein the voltage conversion module comprises:
   a DC/DC voltage converter having a feedback terminal and an output terminal to output the converted voltage;
   a feedback resistor coupling the voltage output terminal with the feedback terminal; and
   a variable resistor coupling the feedback terminal to a reference; and wherein the converted voltage is based on the resistance value of the feedback resistor and the resistance value of the variable resistor.

6. The system of claim 5, wherein the first control signal comprises a value of the variable resistor for outputting the desired amplitude of the stimulation signal and wherein the value of the variable resistor is varied in time according to the received first control signal.

7. The system of claim 3, wherein the at least one set of stimulation parameters further comprise a desired period and a desired pulse width of the stimulation signal and wherein the second control signal is adjusted based on the desired period and pulse width.

8. The system of claim 7, wherein the at least one switch comprises a MOSFET switch and the driver comprises a MOSFET driver.

9. The system of claim 1, wherein the voltage conversion module is configured to convert the supply voltage to a positive converted voltage and a negative converted voltage; and
   wherein the at least one switch comprises:
      a first switch receiving the positive converted voltage and selectively outputting based on the second control signal the positive converted voltage at an output terminal; and
      a second switch receiving the negative converted voltage and selectively outputting based on the second control signal the negative converted voltage at the output terminal.

10. The system of claim 9, wherein the controller unit is configured to operate as a finite state machine having at least an inter pulse state, a positive pulse state, and a negative pulse state, wherein
   in the positive pulse state the controller unit is configured to output the second control signal to configure the first switch to the closed position and maintain the second switch in the open position to output a positive pulse in the stimulation signal;
   in the negative pulse state the controller unit is configured to output the second control signal to configure the second switch to the closed position and maintain the first switch in the open position to output a negative pulse in the stimulation signal; and
   in the inter pulse state the controller unit is configured to output the first and second control signals to maintain the first switch in the open position and the second switch in the open position to output no pulses in the stimulation signal.

11. The system of claim 9, wherein when the first switch is closed the second switch is open to output the positive converted voltage as the stimulation signal and wherein when the second switch is closed the first switch is opened to output the negative converted voltage as the stimulation signal.

12. The system of claim 9, wherein the voltage conversion module comprises a dual DC/DC converter that is configured to output the positive converted voltage from a first output terminal and the negative converted voltage from a second output terminal;
   wherein the first output terminal is coupled to a first feedback terminal of the convertor via a first feedback resistor, the first feedback terminal being further coupled to a reference voltage via a first variable resistor, and the positive converted voltage is based on the resistance value of the first feedback terminal and the resistance value of the first variable resistor; and
   wherein the second output terminal is coupled to a second feedback terminal of the convertor via a second feedback resistor, the second feedback terminal being further coupled to the reference voltage via a second variable resistor, and the negative converted voltage being based on the resistance value of the second feedback terminal and the resistance value of the second variable resistor.

13. The system of claim 9, wherein the at least one set of stimulation parameters comprises a desired pulse width of the stimulation signal and wherein the second control signal is adjusted based on the desired pulse width;
   wherein the first switch outputs the positive converted voltage at the output terminal for a duration of time corresponding to the desired pulse width; and
   wherein the second switch outputs a negative discharging pulse immediately after the first switch completes outputting the positive converted voltage, whereby the negative discharging pulse shortens a voltage fall time at the output terminal.

14. The system of claim 13, wherein the width of the negative discharging pulse is chosen based on the amplitude of the positive converted voltage outputted by the first switch, the width of the negative discharging pulse being shorter than the desired pulse width.

15. The system of claim 14, wherein the at least one set of stimulation parameters comprises a desired amplitude, a desired rise time, a desired hold time, a desired drop time, and a desired idle time of a cycle of the stimulation signal; and
   wherein a plurality of negative discharging pulses are defined in the second control signal, each discharging pulse being defined based on an amplitude of the stimulation signal at a corresponding point in time within the cycle of the stimulation signal.

16. The system of claim 15, wherein the second control signal comprises:
   a first switch control signal for controlling the first switch, the first switch control signal defining a desired period, a desired pulse width, and a plurality of positive discharging pulse widths for a cycle of the stimulation signal; and
   a second switch control signal for controlling the second switch, the second switch control signal defining a desired period, a desired pulse width, and a plurality of negative discharging pulse widths for a cycle of the stimulation signal;
   wherein at least one of the first switch control signal and the second switch control signal further defines a phase offset.

17. The system of claim 9, wherein the controller unit is configured to operate as a finite state machine having at least a positive pulse state, a positive discharge state, a negative pulse state, and a negative discharge state wherein
   in the positive pulse state the controller unit is configured to output the second control signal to configure the first switch to the closed position and maintain the second switch in the open position to output a positive pulse in the stimulation signal;
   in the positive discharge state the controller unit is configured to output the second control signal to open the first switch, immediately close the second switch following opening of the first switch, open the second switch after a duration of time corresponding to a negative discharging pulse width to reduce the fall time of the positive pulse in the stimulation signal;

in the negative pulse state the controller unit is configured to output the second control signal to configure the second switch to the closed position and maintain the first switch in the open position to output a negative pulse in the stimulation signal; and in the negative discharge state the controller unit is configured to output the second control signal to open the second switch, immediately close the first switch following opening of the second switch, open the first switch after a duration of time corresponding to a positive discharging pulse width to reduce the fall time of the negative pulse in the stimulation signal.

18. The system of claim 17, wherein the negative discharging pulse width is chosen based on the amplitude of the positive converted voltage outputted by the first switch during the previous positive pulse state and wherein the positive discharging pulse width is chosen based on the amplitude of the negative converted voltage outputted by the second width during the previous negative pulse state.

19. The system of claim 17, wherein the first switch comprises an opto-coupler and the second switch comprises an opto-coupler.

20. The system of claim 19, wherein the voltage fall time at the output terminal is no more than approximately 50 µs.

21. The system of claim 1, wherein the controller unit is further configured to receive a mode signal indicating that a particular set of the stimulation parameters is to be selected, and wherein the plurality of stimulation control signals are generated based on the selected set of stimulation parameters.

22. The system of claim 1, wherein a change in the trigger signal indicates a change in the position of the user and that a particular set of the stimulation parameters is to be selected, and wherein the plurality of stimulation control signals are generated based on the selected set of stimulation parameters.

23. A method for generating a stimulation signal for a functional electrical stimulation system, the method comprising:

receiving a selection of a set of stimulation parameters defining characteristics of the stimulation signal to be generated;

determining values of a first control signal and a second control signal based on the set of stimulation parameters;

outputting the first control signal to control an amplitude of the stimulation signal;

determining a state of a finite state machine; and outputting a second control signal based on the state of the state machine, the second control signal being adapted for controlling timing for the stimulation signal.

24. The method of claim 23, wherein the set of stimulation parameters comprise a desired amplitude of the stimulation signal, and the first control signal is determined based on the desired amplitude.

25. The method of claim 24, wherein the set of stimulation parameters further comprise a desired rise time, a desired hold time, a desired drop time, and a desired idle time of a cycle of the stimulation signal, and the first control signal is determined based on the desired rise, desired hold time, desired drop time and desired idle time.

26. The method of claim 25, wherein the set of stimulation parameters comprise a desired period and a desired pulse width of the stimulation signal, and the second control signal is determined based on the desired period and pulse width.

27. The method of claim 26, wherein the finite state machine comprises an inter pulse state, a positive pulse state, and a negative pulse state, wherein in the positive pulse state the second control signal configures a first switch to a closed position and maintains a second switch in an open position to output a positive pulse in the stimulation signal;

in the negative pulse state the second control signal configures the second switch to the closed position and maintains the first switch in the open position to output a negative pulse in the stimulation signal; and in the inter pulse state the first and second control signals maintain the first switch in the open position and the second switch in the open position to output no pulses in the stimulation signal.

28. The method of claim 26, wherein the finite state machine comprises a positive pulse state, a positive discharge state, a negative pulse state, and a negative discharge state wherein in the positive pulse state the second control signal configures a first switch to a closed position and maintains a second switch in an open position to output a positive pulse in the stimulation signal;

in the positive discharge state the second control signal configures the first switch to the open position, immediately configures the second switch to the closed position following the opening of the first switch, and configures the second switch to the open position after a duration of time corresponding to a negative discharging pulse width to reduce the fall time of the positive pulse in the stimulation signal;

in the negative pulse state the second control signal configures the second switch to the closed position and maintains the first switch in the open position; and in the negative discharge state the second control signal configures the second switch to the open position, immediately configures the first switch to the closed position following the opening of the second switch, and configures the first switch to the open position after a duration of time corresponding to a positive discharging pulse width to reduce the fall time of the negative pulse in the stimulation signal.

29. An electrical stimulation system for generating a stimulation signal for at least two electrodes coupled to a body part in a functional electrical stimulation system, the electrical stimulation system comprising:

a controller unit operable for receiving at least one set of stimulation parameters, receiving a trigger signal; and in response to receiving the trigger signal, outputting at least a first control signal and a second control signal based on the at least one set of stimulation parameters;

a voltage conversion module coupled to the controller unit, the voltage conversion module configured to receive at least the first control signal and converting a supply voltage based on the received first control signal to a positive converted voltage and a negative converted voltage;

a first switch configured to receive the positive converted voltage and selectively outputting based on the second control signal the positive converted voltage at a stimulation output terminal; and a second switch configured to receive the negative converted voltage and selectively outputting based on the second control signal the negative converted voltage at the stimulation output terminal.

30. The electrical stimulation system of claim 29, wherein the controller unit is configured to operate as a finite state machine having at least an inter pulse state, a positive pulse state, and a negative pulse state, wherein in the positive pulse state the controller unit is configured to output the second control signal to configure the first switch to the closed position and maintain the second switch in the open position to output a positive pulse in the stimulation signal;

in the negative pulse state the controller unit is configured to output the second control signal to configure the second switch to the closed position and maintain the first switch in the open position to output a negative pulse in the stimulation signal; and in the inter pulse state the controller unit is configured to output the first and second control signals to maintain the first switch in the open position and the second switch in the open position to output no pulses in the stimulation signal.

31. The electrical stimulation system of claim 29, wherein the controller unit is configured to operate as a finite state machine having at least a positive pulse state, a positive discharge state, a negative pulse state, and a negative discharge state wherein in the positive pulse state the controller unit is configured to output the second control signal to configure the first switch to the closed position and maintain the second switch in the open position to output a positive pulse in the stimulation signal;

in the positive discharge state the controller unit is configured to output the second control signal to open the first switch, immediately close the second switch following opening of the first switch, open the second switch after a duration of time corresponding to a negative discharging pulse width to reduce the fall time of the positive pulse in the stimulation signal;

in the negative pulse state the controller unit is configured to output the second control signal to configure the second switch to the closed position and maintain the first switch in the open position to output a negative pulse in the stimulation signal; and in the negative discharge state the controller unit is configured to output the second control signal to open the second switch, immediately close the first switch following opening of the second switch, open the first switch after a duration of time corresponding to a positive discharging pulse width to reduce the fall time of the negative pulse in the stimulation signal.

32. A computer readable medium comprising a plurality of instructions executable on a processor of a device for adapting the processor to implement a method of generating a stimulation signal for a functional electrical stimulation system, the computer readable medium comprising instructions for:

receiving a selection of a set of stimulation parameters defining characteristics of the stimulation signal to be generated;

determining values of a first control signal and a second control signal based on the set of stimulation parameters;

outputting the first control signal to control an amplitude of the stimulation signal;

determining a state of a finite state machine; and outputting a second control signal based on the state of the state machine, the second control signal being adapted for controlling timing for the stimulation signal.

* * * * *